US008162890B2

(12) United States Patent
Amisar et al.

(10) Patent No.: US 8,162,890 B2
(45) Date of Patent: Apr. 24, 2012

(54) CATHETER INSERTION APPARATUS AND METHOD OF USE THEREOF

(75) Inventors: Shai Amisar, Tel-Aviv (IL); Ronen Radomski, Haifa (IL)

(73) Assignee: Flexicath Ltd., Haifa (IL)

( * ) Notice: Subject to any disclaimer, the term of this patent is extended or adjusted under 35 U.S.C. 154(b) by 60 days.

(21) Appl. No.: 12/227,357

(22) PCT Filed: May 6, 2007

(86) PCT No.: PCT/IL2007/000552
§ 371 (c)(1),
(2), (4) Date: Aug. 11, 2009

(87) PCT Pub. No.: WO2007/132444
PCT Pub. Date: Nov. 22, 2007

(65) Prior Publication Data
US 2009/0306591 A1    Dec. 10, 2009

Related U.S. Application Data

(60) Provisional application No. 60/800,413, filed on May 16, 2006, provisional application No. 60/902,049, filed on Feb. 20, 2007.

(51) Int. Cl.
*A61M 5/178* (2006.01)
(52) U.S. Cl. .................................. 604/164.01
(58) Field of Classification Search .................... 604/122
See application file for complete search history.

(56) References Cited

U.S. PATENT DOCUMENTS

| 2,937,643 A | 10/1957 | Elliot |
| 3,185,151 A | 5/1965 | Czorny |
| 3,547,119 A * | 12/1970 | Hall et al. ................. 604/164.04 |
| 3,782,383 A * | 1/1974 | Thompson et al. ............ 604/177 |
| 4,417,886 A * | 11/1983 | Frankhouser et al. ........ 604/510 |
| 4,473,067 A | 9/1984 | Schiff |
| 4,689,047 A | 8/1987 | Bauer |
| 4,997,421 A * | 3/1991 | Palsrok et al. ................. 604/174 |

(Continued)

FOREIGN PATENT DOCUMENTS
WO        03/084428        10/2003
(Continued)

OTHER PUBLICATIONS

International Search Report for PCT/IL2007/000552, mailed Jul. 28, 2008.

(Continued)

*Primary Examiner* — Nicholas Lucchesi
*Assistant Examiner* — Jason Flick
(74) *Attorney, Agent, or Firm* — Nixon & Vanderhye P.C.

(57) ABSTRACT

The invention relates to a catheter insertion system utilizing a catheter introducer device having an introducer sheath, the catheter insertion system comprise a catheter containment unit in which a catheter tube having a catheter hub is held, said catheter containment unit comprises an opening adapted to sealably and reversibly connect to an inserter head, said inserter head is adapted to sealably and reversibly connect, and provide said catheter tube passage, to said catheter introducer device, wherein said catheter containment unit comprises at least one flexible portion and an elastic/resilient portion located near its opening for advancing portions of said catheter tube through said passage, and wherein said inserter head is adapted to sealably receive a portion of said catheter hub in a socket provided therein.

33 Claims, 14 Drawing Sheets

U.S. PATENT DOCUMENTS

| | | | |
|---|---|---|---|
| 5,114,256 A | 5/1992 | Lin | |
| 5,125,911 A | 6/1992 | Grabenkort et al. | |
| 5,141,497 A | 8/1992 | Erskine | |
| 5,250,033 A | 10/1993 | Evans et al. | |
| 5,737,803 A | 4/1998 | Tisdale | |
| 5,755,693 A | 5/1998 | Walker et al. | |
| 5,788,675 A | 8/1998 | Mayer | |
| 6,001,080 A | 12/1999 | Kuracina et al. | |
| 6,558,354 B1 * | 5/2003 | Howell | 604/162 |
| 6,866,650 B2 | 3/2005 | Stevens et al. | |
| 2001/0044591 A1 | 11/2001 | Stevens et al. | |
| 2004/0167561 A1 | 8/2004 | Boucher et al. | |
| 2007/0299460 A9 | 12/2007 | Boucher et al. | |
| 2008/0132880 A1 * | 6/2008 | Buchman | 604/533 |
| 2009/0054845 A1 * | 2/2009 | Puhasmagi et al. | 604/180 |

FOREIGN PATENT DOCUMENTS

| | | |
|---|---|---|
| WO | 2006/085331 | 8/2006 |
| WO | 2007/052278 | 5/2007 |

OTHER PUBLICATIONS

Written Opinion for PCT/IL2007/000552, mailed Jul. 28, 2008.

* cited by examiner

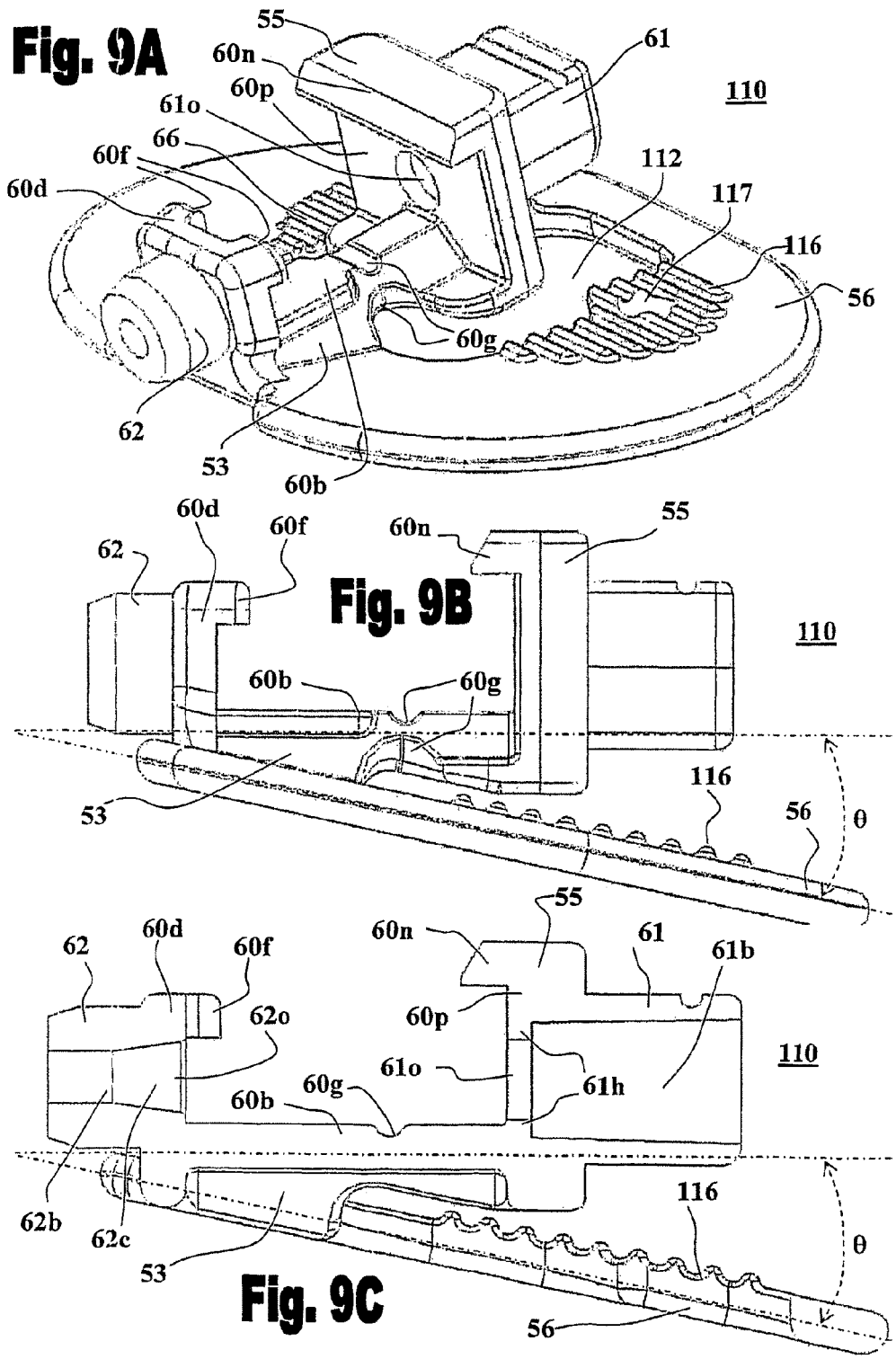

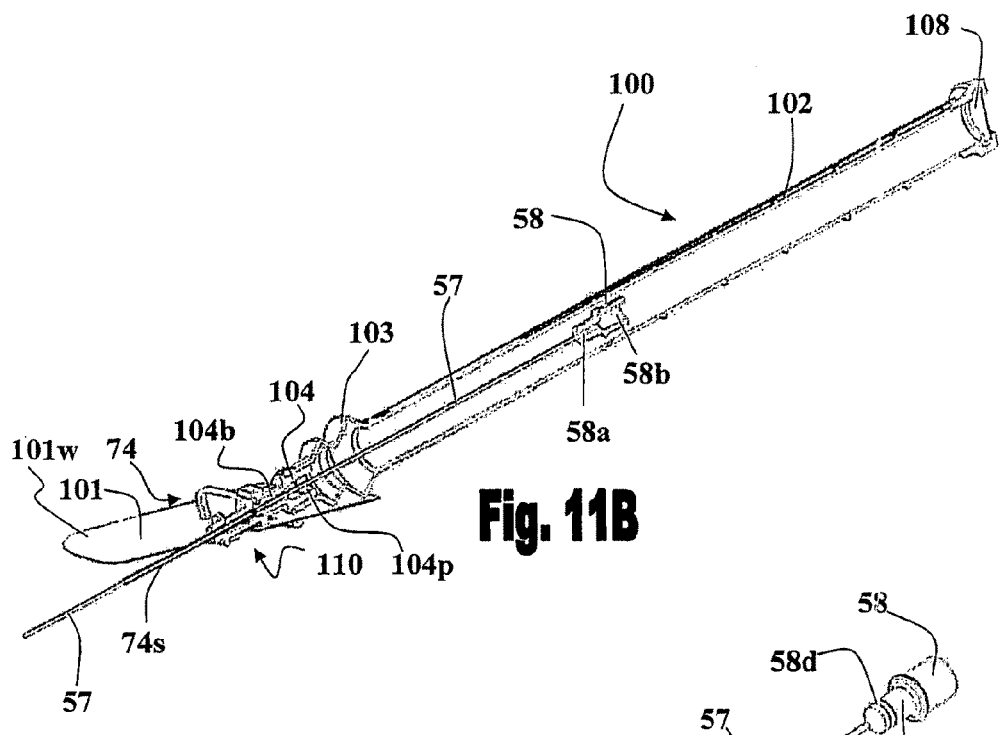
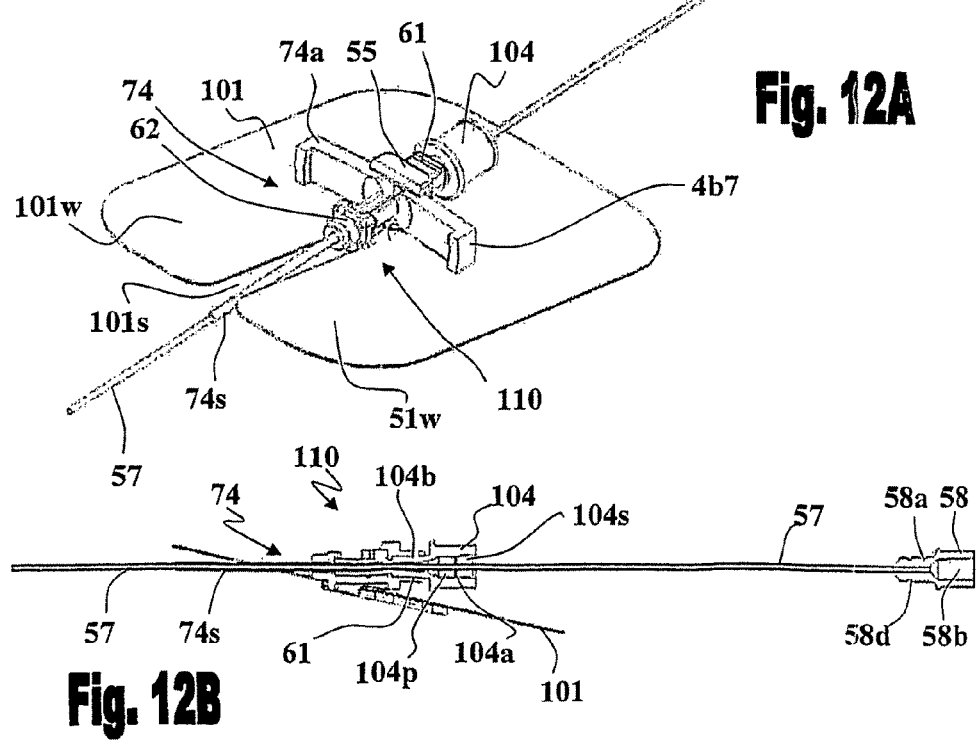

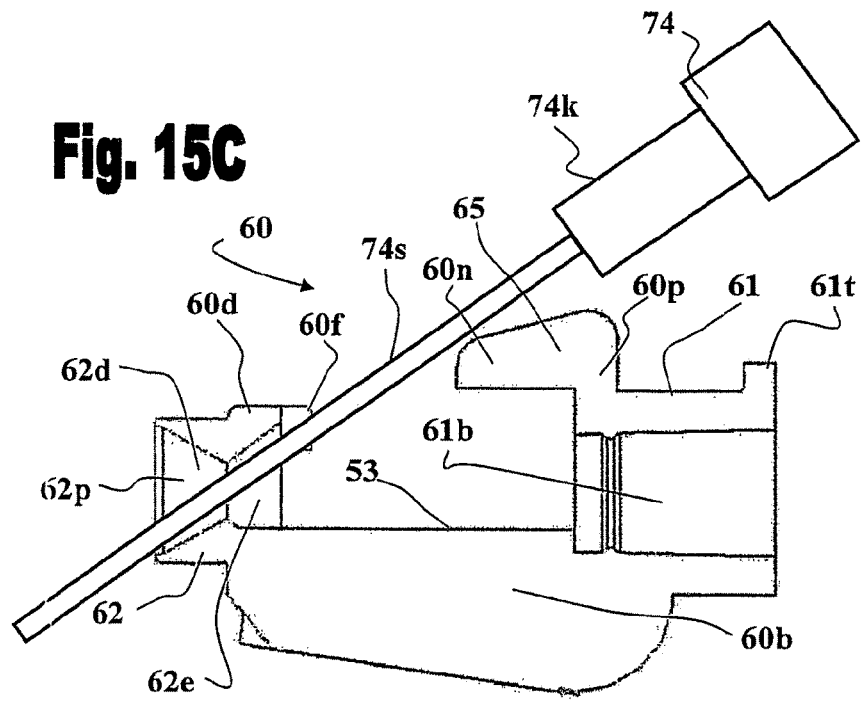
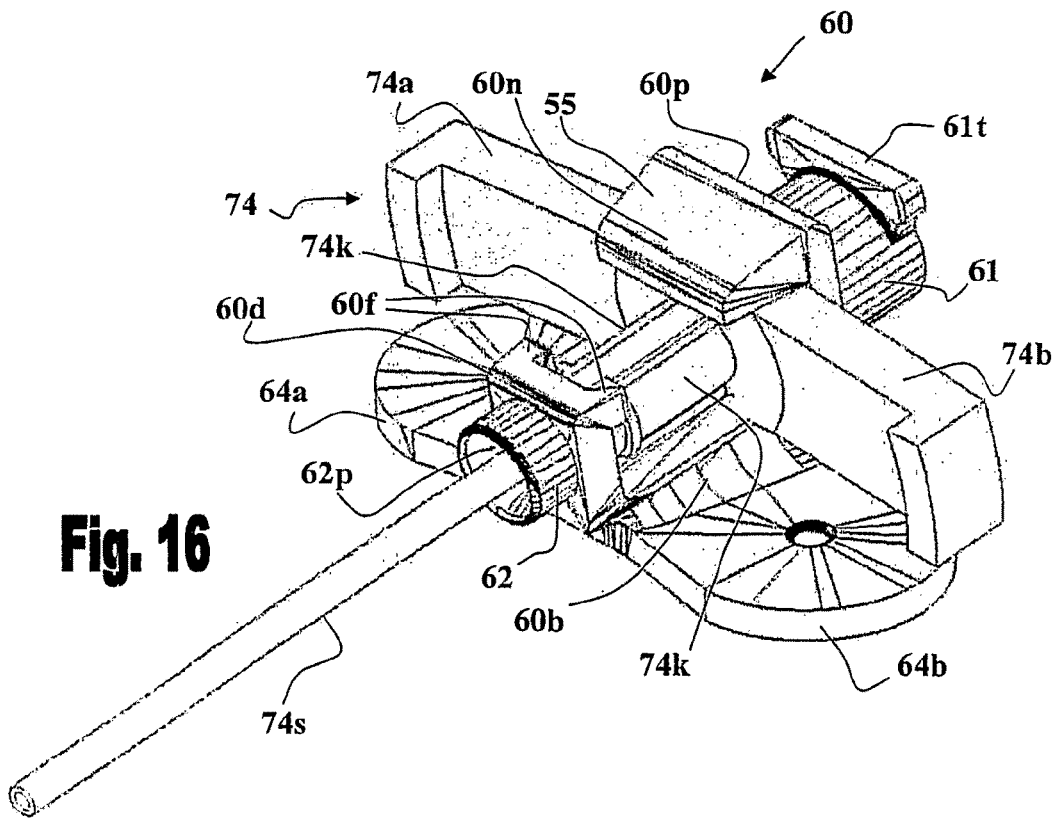

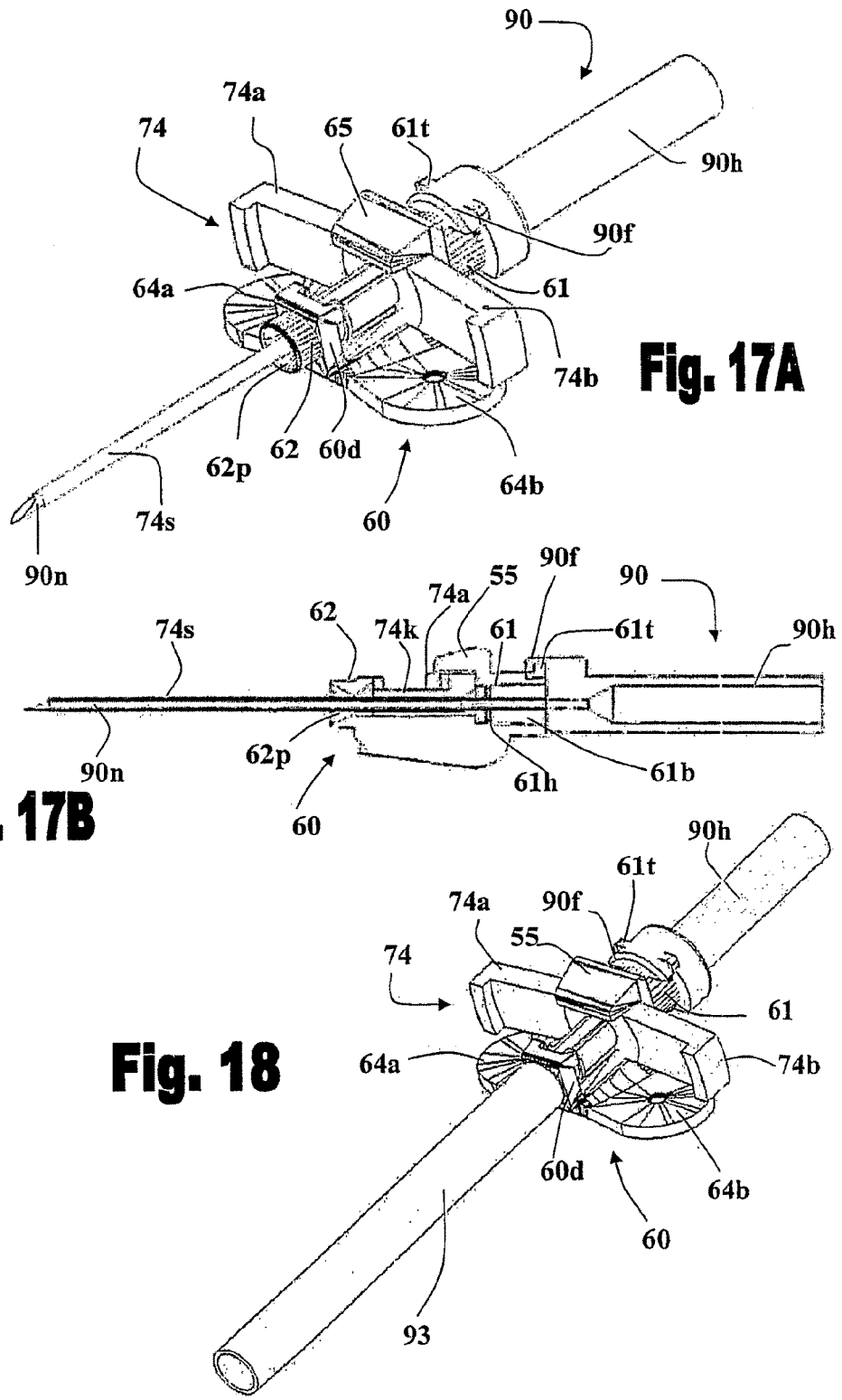

CATHETER INSERTION APPARATUS AND METHOD OF USE THEREOF

This application is the U.S. national phase of International Application No. PCT/IL2007/000552 filed 6 May 2007 which designated the U.S. and claims priority to U.S. Application No(s). 60/800,413, filed 16 May 2006 and 60/902,049, filed 20 Feb. 2007, the entire contents of each of which are hereby incorporated by reference.

FIELD OF THE INVENTION

The present invention relates to an apparatus and method for inserting a catheter device into the body of a treated subject. More particularly, the invention relates to a catheter insertion system comprising removable and non-removable elements, and to a method of use thereof, for inserting an intravenous catheter device into the body of a treated subject while maintaining sterile surroundings and preventing movements of the catheter device after its insertion.

BACKGROUND OF THE INVENTION

Catheterization procedures are typically used when frequent or continuous injections of medications or fluids for nutritional support are provided to a patient. When a long treatment period is required (e.g., longer than 3 days) a long (6 cm or longer) and soft catheter is usually used, which allows maintaining it in the body of the treated subject up to several months.

For instance, in intravenous catheterization procedures a single puncture of a blood vessel is made for inserting and advancing the catheter device towards a selected location in a vessel wherein it is left for periodic use. In this way repetitive piercing of patient's vessels is avoided. Intravenous catheter insertion devices are typically designed to allow inserting the catheter while preserving a sterile environment and preventing the passage of blood out via the catheter insertion apparatus.

The insertion of many intravenous catheters is carried out by placing an introducer catheter comprising an introducer needle for making the puncture (over-the-needle). After the introducer catheter is placed in the target vessel the introducer needle is withdrawn therefrom and the catheter tube may be then inserted therethrough into the selected vascular location.

In some catheterization procedures a removable introducer, such as the peelable introducer (e.g., Peel-Away®), is used in the insertion step. For example, the Peel-Away® introducer consists of a disposable sheath needle having two opposing tearing tabs attached to its proximal end (i.e., trailing end). The insertion of the Peel-Away® introducer into the vessel is done in much the same way as the over-the-needle procedure i.e., first the blood vessel is punctured by the introducer needle contained within the needle sheath and thereafter the introducer unit is advanced into the vessel, the introducer needle is then removed, and the catheter tube is inserted into the selected vascular location. The catheter insertion step is usually carried out by pushing the catheter tube manually via an entry port of the introducer.

After the catheter tube is placed in the vessel the needle sheath is removed, by retracting it from the patient's vessel and peeling it off the catheter by grasping its tearing tabs and pulling them laterally in opposite directions, thereby tearing the needle sheath apart along its longitudinal length.

The relatively long periods of time during which the catheter remains in its position in the patient's vein may cause catheter related infections. These infections are typically caused by chemical irritation, contamination of the catheter during its insertion, or by organisms dwelling on the skin of the patient that enter the punctured vein through the outer surface of the catheter due to catheter movement in or out of the insertion site.

An intravenous catheter assembly is described in WO 03/084428 wherein a sterile catheter insertion apparatus comprised of an integral sterile sheath comprising the catheter tube therein is used. Various catheter insertion apparatuses are also described in WO 06/085331, the disclosure of which is incorporated herein by reference, wherein the catheter tube contained in a flexible sleeve is inserted into the patient's vessel by utilizing catheter advancing means. However, the above mentioned catheter insertion apparatuses are designed for insertion using the conventional over-the-needle technique wherein the catheter introducer remains in the punctured vessel during the entire procedure.

Catheter insertion procedures in which a peelable introducer is utilized for introducing the catheter tube into the body of the treated subject involves proximal and distal movement of the catheter tube, particularly after completing the insertion of the catheter tube and retracting the peelable introducer proximally for removing it from the vessel and splitting it. Undesirably, during these steps a potion of the catheter tube is left out of the patient's body which requires either introducing said portion through the skin without the introducer, or leaving it exposed on the skin susceptible for kinking and snagging. Additionally, catheter insertion devices utilizing peelable introducers, and procedures employing said devices, do not provide means for securing the peelable sheath of said peelable introducer and for securely splitting said sheath during its retraction from the patient's body.

The catheter insertion procedures of the prior art have not yet provided satisfactory solutions for inserting a catheter tube into the body of the treated subject using a catheter introducer while maintaining sterile surroundings, and for preventing the displacement and contamination of the catheter tube near the site of insertion into the body of the treated subject.

It is therefore an object of the present invention to provide a method and apparatus for inserting a catheter tube into the body of a treated subject by means of a catheter introducer while maintaining the catheter tube within sterile surroundings.

It is another object of the present invention to provide a method and apparatus for inserting a catheter tube into the body of a treated subject by means of a catheter introducer while maintaining sterile surrounding about the insertion site.

It is a further object of the present invention to provide simplified method and apparatus for securely inserting a catheter tube into the body of a treated subject by means of a catheter introducer, wherein the catheter tube is kept in a removable sterile environment maintaining means.

It is yet another object of the present invention to provide simplified method and apparatus for placing a catheter tube by means of a peelable introducer, for removing said peelable introducer and maintaining said catheter tube in place while preventing the kinking of the catheter tube near the insertion site It is yet a further object of the present invention to provide simplified method and apparatus for placing a catheter tube by means of a peelable introducer, wherein the catheter tube is protected from direct contact throughout the treatment process, and wherein portions of the catheter tube may remain untouchably outside the body of the treated subject.

It is yet a further object of the present invention to provide simplified method and apparatus for placing a catheter tube by means of a standard catheter introducer device, wherein the catheter tube is protected from direct contact throughout the treatment process, and wherein portions of the catheter tube may remain untouchably outside the body of the treated subject.

An additional object of the present invention is to provide a device for placing a catheter tube by means of a peelable introducer, and for maintaining said catheter tube in place during the provision of medication.

Other objects and advantages of the invention will become apparent as the description proceeds.

SUMMARY OF THE INVENTION

The inventors of the present invention discovered that catheterization procedures utilizing catheter introducer devices can be performed while maintaining sterile surroundings about the insertion site and preventing unnecessary catheter movements in or out of the patient's body by utilizing a catheter insertion system configured to provide sealed connection to the catheter introducer device and allow advancing the catheter tube therethrough while maintaining the same sealed and sterile therein. In addition, the catheter insertion system of the present invention advantageously facilitates the removal of removable catheter introducers while minimizing catheter displacements during its removal.

The catheter insertion apparatus of the invention generally comprises a catheter containment unit comprising the catheter tube, said catheter containment unit comprises an opening adapted to sealably and reversibly connect to an inserter head, wherein said inserter head is adapted to provide sealable and reversible connection and passage to a catheter introducer device, preferably a removable catheter introducer device, directly or via connection means, preferably by means of a removable adapter configured to hold said introducer and provide a convenient connection and passage thereto.

The term "catheter containment unit" refers to a vessel suitable for holding a catheter tube having a catheter hub (entry port) therein and prevent direct contact therewith. The term removable catheter introducer device generally refers to a catheter introducing device (e.g., peelable introducers) having a proximal and distal portions, said distal portion comprises an introducer sheath (i.e., the needle sheath) designed to be positioned in the body of a treated subject, to provide passage thereinto for advancing a catheter tube therethrough, and that can be removed from the body of treated subject and from the catheter tube passing therethrough thereafter by means of tearing tabs provided on the proximal portion. The term inserter head generally refers herein to a connecting element having an internal passage adapted for passage of a catheter tube thereinside, said inserter head is used for connecting between the interior of a catheter containment unit connected to one end thereof and to the passage of an introducer sheath of a removable introducer attached to the other end of the inserter head.

In one aspect the present invention is directed to a catheter insertion system utilizing a catheter introducer device, preferably a removable catheter introducer device (e.g., peelable introducer), the catheter insertion system comprises a catheter containment unit having an opening sealably and reversibly connected to an inserter head adapted to sealably and reversibly connect and provide passage to said catheter introducer device by means of an adapter holding said catheter introducer device. Preferably, the inserter head is adapted to sealably receive the hub of the catheter tube in a socket provided in its proximal portion. Advantageously, the adapter is designed to allow removal of a removable introducer device held by it by simultaneously retracting and splitting portions of the splittable sheath of said removable introducer device. Advantageously, the catheter containment unit comprises at least one flexible portion.

The catheter insertion system may further comprise a stiffening guide-wire removably placed in, to fill, the lumen of the catheter tube.

In a preferred embodiment of the invention the adapter comprises a "U"-like shaped portion having substantially parallel distal and proximal arms having an inner (facing) and outer sides, said arms are connected by a base and comprise opposing (facing) apertures, wherein said "U"-like shaped portion is configured to receive and hold the catheter introducer device such that the proximal portion of said catheter introducer device is held by said arms, at least a portion of the introducer sheath at the distal portion of said catheter introducer device is passed through the aperture provided in said distal arm, and the interior of said introducer sheath is accessible via the aperture provided in said proximal arm of said "U"-like shaped portion.

Retaining means are preferably provided in the distal and/or proximal arms of said "U"-like shaped portion for fastening the proximal portion of the catheter introducer device. The outer side of the proximal and/or distal arms preferably comprises hollow quick connecting means allowing sealable and reversible connection thereto while providing passage therethrough to/from the apertures provided in said arms.

Advantageously, the aperture provided in the distal arm of the "U"-like shaped portion is adapted to prevent the splitting of the portion, or entire length, of the introducer sheath passed therethrough, and facilitate splitting portions of said introducer sheath within the "U"-like shaped portion.

The proximal and distal arms of the "U"-like shaped portion of the adapter may comprise slits passing from an upper side thereof and connected to the apertures provided in said arms to allow removal of a catheter tube passing through said apertures via said slits. If said arms comprise hollow connecting means corresponding slits may be provided thereon passing from an upper side thereof and connected to their hollow interiors. The base connecting said arms may comprise lateral upper, and/or lower, grooves for increasing its elasticity/flexibility and allowing reversibly bending said base.

The passage through the aperture in the distal arm and the hollow interior of connecting means provided on the outer side of said distal arm is preferably distally tapering. At least a portion of the passage through the hollow interior of the connecting means provided on the outer side of the distal arm may also taper proximally.

The adapter may further comprise a base portion or wings to which said "U"-like shaped portion is connected to allow easy and comfortable attachment thereof to the body of the treated subject. The connection between said base portion or wings and said "U"-like shaped portion is advantageously achieved by means of an elastic or flexible member thereby allowing reversibly tilting said "U"-like shaped portion thereabout. The connection between said base portion and said "U"-like shaped portion is preferably provided at distal sections of said portions and configured such that an acute angle (e.g., ~12°) is obtained therebetween, thereby allowing downward bending of the proximal portion of said "U"-like shaped portion towards said base portion. Conveniently, said base portion comprise an opening adapted in location and size to allow passage of the proximal portion of said "U"-like shaped portion therethrough when it is bent downwardly.

Advantageously, the catheter containment unit comprises an elastic/resilient portion located near its opening and configured to allow the advancing of portions of the catheter tube by externally grasping said catheter tube via said catheter containment unit and pushing the same distally such that said elastic/resilient portion is pressed against the inserter head connected thereto, elastic/resilient portion of said catheter containment unit collapse, and portions of catheter tube are advanced distally via the passage provided in said inserter head, wherein the shape of said elastic/resilient portion is restored when the applied grasp is released. The catheter containment unit may include filter means for allowing passage of air to its interior while preventing contamination thereof. Preferably, the filtering means is a type tortuous path filtering means. Additionally or alternatively, said catheter containment unit may comprise a compliant or corrugated portion adapted to expand in response to pressure buildups in the catheter containment unit due to contractions of the elastic/resilient portion, and to restore its shape when the contraction of said elastic/resilient is released.

Advantageously, the size and/or thickness of a distal portion of the elastic/resilient portion of the catheter containment device is made smaller than the size/thickness of the proximal portion thereof.

Optionally, a disinfecting element containing an antimicrobial substance is placed over a portion of the catheter tube adjacent to the insertion site.

The method for inserting the catheter tube by means of the catheter insertion system of the invention utilizing a catheter introducer device, preferably a removable catheter introducer device, generally comprises the following steps: placing the introducer sheath in the body of the treated subject by means of a piercing needle; removing the piercing needle; connecting a catheter containment unit comprising said catheter tube to said catheter introducer device by means of an inserter head adapted to fit into its opening; advancing said catheter tube into the body of the treated subject; optionally, retaining the entry port of said catheter tube in the a socket provided in said inserter head; removing said catheter containment unit by pulling it proximally and releasing its grip over said inserter head; and if a removable catheter introducer device is used, optionally, removing said removable catheter introducer device.

If an adapter is used to facilitate the catheter insertion and the removal of the catheter introducer device, said catheter introducer device is placed in said adapter before placing the piercing needle therein, and the introducer sheath is placed in the body of the treated subject while its proximal portion is held by said adapter. After removal of the piercing needle the catheter containment unit containing the catheter tube and having the inserter head connected thereto is connected to said adapter by means of said inserter head. After completing the insertion procedure and removing the removable catheter introducer device, said adapter, with the proximal portion of the catheter tube passing through the apertures in its arms, and having the inserter head connected thereto, is affixed to the body of the treated subject, thereby affixing and protecting said proximal catheter tube portion.

Preferably, the adapter comprises a "U"-like shaped portion, having two substantially parallel arms, adapted to receive and hold the catheter introducer device. Most preferably, the catheter introducer device is a type of removable adapter, wherein said catheter insertion device is removed after completing the catheter insertion steps by splitting portions of the introducer sheath within the "U"-like shaped portion.

If the arms of said adapter, and any connectors which may be provided on the outer sides of said arms, comprise slits, the catheter insertion procedure may further comprise a step of removing said adapter by disconnecting the inserter head and removing the catheter tube passing through the apertures provided in said arms, and through said connectors, via said slits.

In another aspect, the present invention is directed to an adapter for a catheter introducer device, preferably a removable catheter introducer device, having an introducer sheath, said adapter comprising: a "U"-like shaped portion having substantially parallel distal and proximal arms, each of which having inner and outer sides; a base for connecting said arms; opposing apertures provided in said arms; wherein said "U"-like shaped portion is adapted to receive and hold said catheter introducer device such that the proximal portion of said removable introducer is held by said arms, the introducer sheath of said catheter introducer device is passed through the aperture provided in said distal arm, and the interior of said introducer sheath is accessible via the aperture provided in said proximal arms of said "U"-like shaped portion.

BRIEF DESCRIPTION OF THE DRAWINGS

The present invention is illustrated by way of example in the accompanying drawings, in which similar references consistently indicate similar elements and in which:

FIGS. 9A to 9E illustrates an adapter for a peelable introducer according to one preferred embodiment of the invention, wherein FIG. 9A is a perspective view, FIG. 9B is a side view, FIG. 9C is a longitudinal-section view, FIG. 9D is a view showing a proximal face, and FIG. 9E is a bottom view, of said adapter;

FIGS. 11A and 11B illustrates perspective and longitudinal-section views, respectively, of the catheter insertion apparatus of the invention using the adapter shown in FIGS. 9A-9E;

FIGS. 12A and 12B illustrates perspective and longitudinal-section views, respectively, of the catheter insertion apparatus of the invention without the flexible sleeve;

FIG. 15C illustrates the assembly of a peelable introducer into the adapter shown in FIGS. 15A-15B;

FIG. 16 shows a perspective view of an assembly of a peelable introducer fitted into the adapter shown in FIGS. 15A-15B;

FIGS. 17A and 17B illustrates perspective and longitudinal-section views, respectively, of an assembly of a peelable introducer fitted into the adapter of the invention and a piercing needle which passes therethrough;

FIG. 18 illustrates an assembly of the peelable introducer fitted into the adapter shown in FIGS. 15A-15B, and a piercing needle passing therethrough, which needle is covered by a needle guard assembly.

DETAILED DESCRIPTION OF PREFERRED EMBODIMENTS

The present invention provides a method and apparatus for inserting a catheter device into the body of a treated subject while maintaining the catheter device in sealed and sterile surroundings. The catheter insertion apparatus of the invention substantially simplifies the catheter insertion procedure particularly when using a peelable introducer and assists in maintaining clean and sterile surroundings during the insertion, the removal of the peelable introducer, and during the entire time period in which the catheter device (catheter tube) is maintained in the body of the treated subject.

Figure 1A:
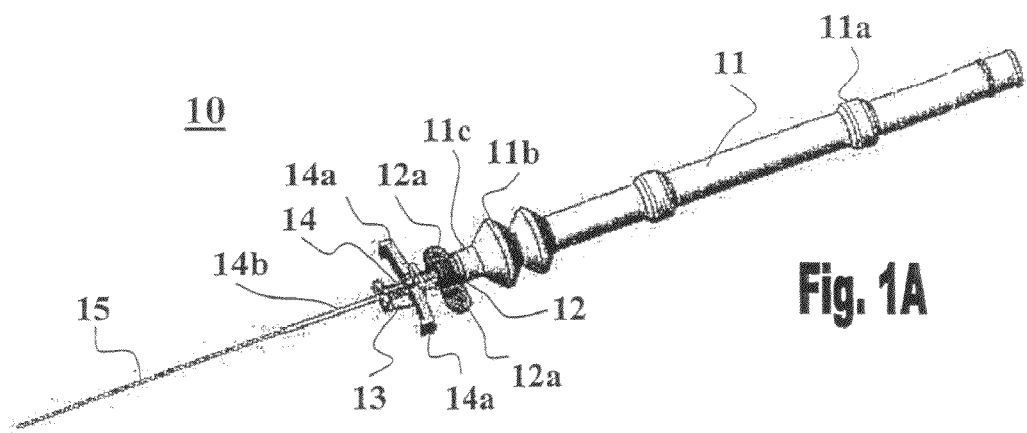
FIG. 1A shows a perspective view of the catheter insertion apparatus of the invention including a peelable introducer and removable adapter.

FIG. 1A shows a perspective view of the catheter insertion apparatus 10 of the invention during the insertion of catheter tube 15. Catheter insertion apparatus 10 comprises a flexible sleeve 11 linked to removable adapter 13 via inserter head 12, attached to a distal opening of said flexible sleeve 11, a peelable introducer 14 assembled in removable adapter 13, and a catheter tube 15 placed in said flexible sleeve 11. Catheter insertion apparatus 10 is configured to allow catheter tube 15 to be advanced distally via a passage (12e, FIG. 1C) provided in inserter head 12 and splittable sheath 14b of peelable introducer 14.

The proximal end of flexible sleeve 11 of catheter insertion apparatus 10 is sealed and its distal end 11c comprises an opening configured to sealably and reversibly connect to inserter head 12. Flexible sleeve 11 may further comprise a resilient/elastic portion 11b provided for facilitating insertion of the catheter tube 15 by grasping lateral sides thereof via flexible sleeve 11, near said resilient/elastic portion 11b, and distally pushing the same distally such that resilient/elastic section 11b is pressed against inserter head 12 while potions of catheter tube 15 are advanced distally via a passage (12e in FIG. 1C) passing inside inserter head 12. Flexible sleeve 11 may also comprise annular supports 11a provided along its length for increasing its stiffness and for preventing kink and collapse thereof.

Inserter head 12 may further comprise lateral retaining wings 12a adapted for attaching the catheter insertion apparatus 10 to the body of the treated subject (not shown). Retaining wings 12a may comprise holes 12h which may be used for anchoring catheter head 12 to the body of the treated subject by sawing an anchoring band therethrough or by using a dedicated adhesive patch (not shown) having two small protruding pegs configure to fit into holes 12h. In a preferred embodiment of the invention inserter head 12 comprises distal connecting means 12c for allowing reversibly connecting it to connecting means provided in a peelable introducer, or to an adapter (13) of such peelable introducer, as shown in FIG. 1C.

Figure 1B:
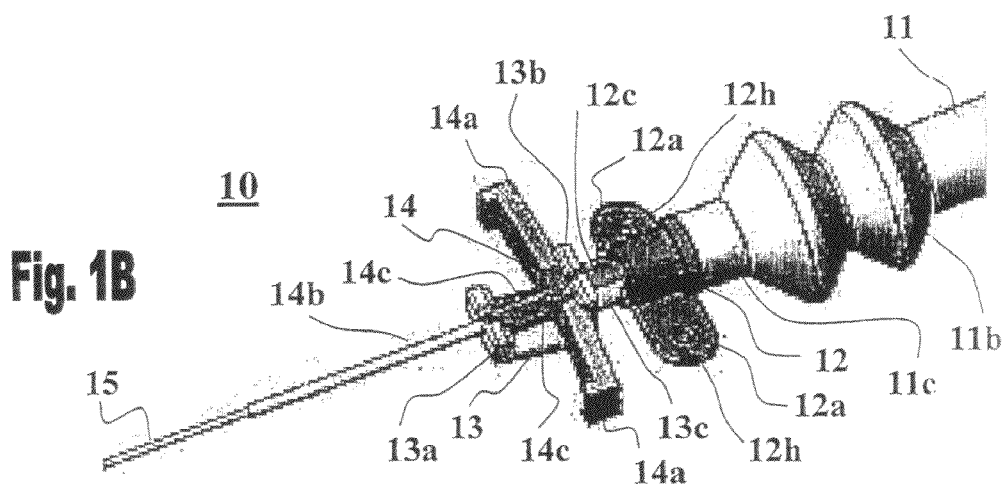
FIG. 1B is a close-up on the distal section of the catheter insertion apparatus of the invention.
Figure 1C:
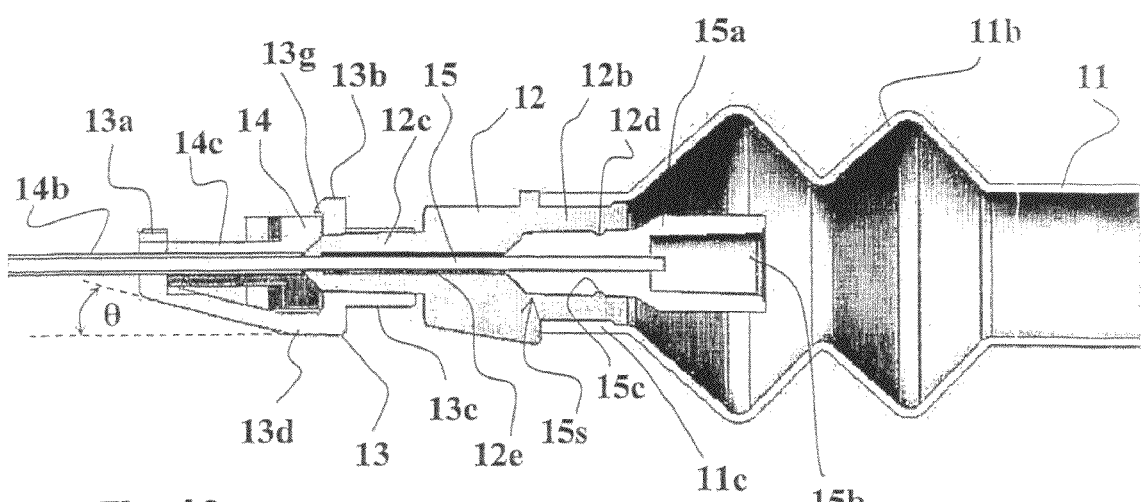
FIG. 1C shows a longitudinal section view of the distal section of the catheter insertion apparatus of the invention after completing the insertion of the catheter tube.

In a preferred embodiment of the invention the proximal end portion 12b of inserter head 12 is adapted to be sealably and reversibly received in the distal end (11c) opening of flexible sleeve 11, as shown in FIG. 1C. Similarly, distal connecting means 12c is adapted to be sealably and reversibly received in quick connector 13c of removable adapter 13. Peelable introducer 14 may be connected to inserter head 12 by means of a suitable adapter, such as removable adapter 13.

Figure 2:
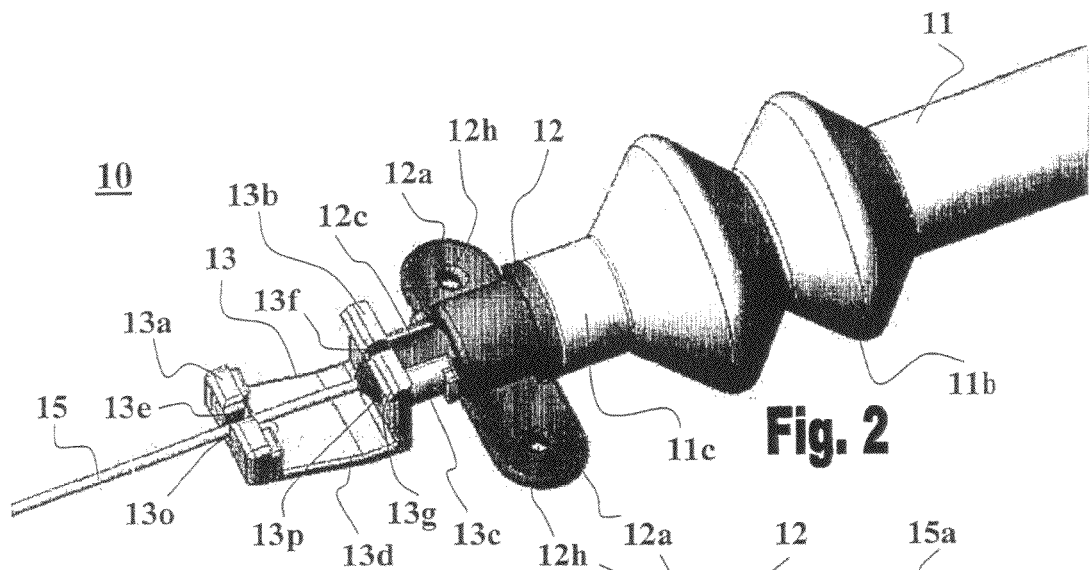
FIG. 2 is a close-up on the distal end section of the catheter insertion apparatus of the invention after removal of the peelable introducer.

In a preferred embodiment of the invention removable adapter 13 is designed to receive the proximal section of the peelable introducer in a "U"-like shaped section thereof, as exemplified in the Figures. With reference to FIG. 2, said "U"-like shaped section may comprise a distal arm 13a connected to a proximal arm 13b, via a base section 13d, where said arms are provided with suitable apertures (13o and 13p, FIG. 2) allowing passage of the splittable sheath 14b of peelable introducer 14 via aperture 13o provided in distal arm 13a, and of catheter tube 15 via aperture 13p provided in proximal arm 13b. Preferably, distal arm 13a comprises a groove (not shown) in its inner side for receiving the distal end tips of shanks 14c of peelable adapter 14, and proximal arm 13b comprises retaining means 13g adapted to retain tearing tabs 14a of peelable introducer 14 and thereby allow snapping it thereinto.

Retaining means 13g is preferably implemented by a relatively short horizontal protrusion (e.g., 1 to 5 mm, preferably about 4 mm) projecting distally on the inner side of proximal arm 13b, at the upper end thereof.

Sealed connection between the inner passage 12e of inserter head 12 and the inner lumen of peelable introducer 14 may be accomplished by configuring distal connecting means 12c of inserter head 12 to be received in the bore provided in quick connector 13c such that its distal tip is engaged inside proximal opening of peelable introducer 14, as demonstrated in FIG. 1C. The distal end section of connecting means 12c thus preferably has a tapering end section.

Figure 3:
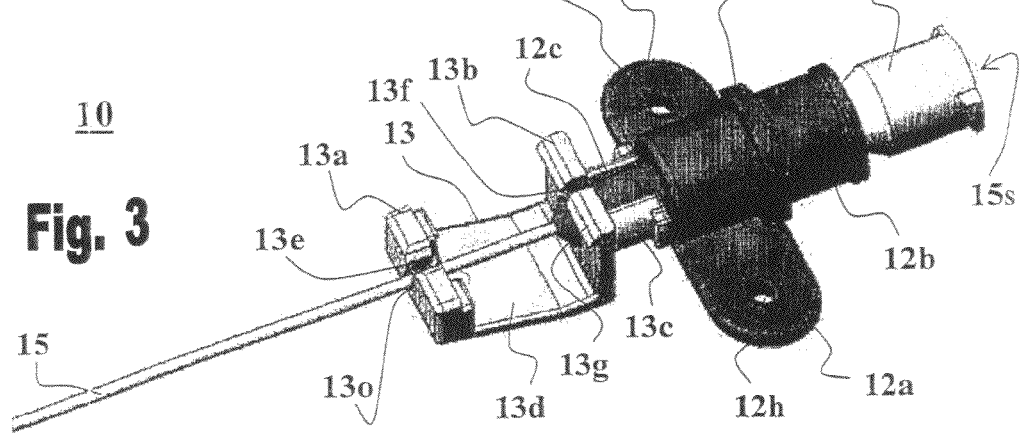
FIG. 3 shows the catheter insertion apparatus of the invention after removal of the peelable introducer and of the flexible sleeve.

Proximal end portion 12b of inserter head 12 includes a socket 15s designed to receive the distal end portion of catheter hub 15a thereinside. As shown in FIG. 1C after insertion of the catheter tube 15 the distal end portion of catheter hub 15a is pressed into the socket 15s provided in proximal section 12b of inserter head 12, thereby sealing its inner passage 12e and forming a composite unit acting as a standard catheter head. In this state flexible sleeve 11 can be removed simply by pulling it proximally and releasing its grip over proximal end portion 12b of inserter head 12. FIG. 3 shows the catheter insertion apparatus of the invention after removal of flexible sleeve 11.

An annular protrusion 12d may be formed on the inner wall of socket 15s of inserter head 12, and configured to tightly fit over a corresponding annular groove 15c formed on the outer surface of catheter entry port 15a when it is pressed into socket 15s of inserter head 12. This locking mechanism provided by fitting annular protrusion 12d over a corresponding annular groove 15c provide further sealing of the inner passage 12e in inserter head 12, which prevents backflow of fluids (e.g., blood) therefrom and eliminates the need for dedicated backflow prevention means, such as valves. Of course, other locking mechanism implementations between inserter head 12 and entry port 15a, equally suitable for blocking fluids backflow, may be provided, for example, an annular groove may provided on the inner wall of socket 15s of inserter head 12 and a corresponding annular protrusion may be provided on the outer surface of catheter entry port 15a.

After attaching entry port 15a and inserter head 12, by clasping the distal end portion of entry port 15a in the socket 15s provided in the proximal section 12b of inserter head 12, the composite unit consisting of inserter head 12 and entry port 15a is attached to the skin of the patient. Inserter head 12 is preferably manufactured from a soft material (e.g., type of silicon) in order to prevent patients' discomfort and the appearance of pressure sores due to long attachment periods of said composite unit to patient's body.

After completing the insertion of the catheter tube 15, peelable introducer 14 may be removed by laterally pulling tearing tabs 14a and gradually splitting and retracting portions of splittable sheath 14b from the body of the patient via aperture 13o (FIG. 2) provided in distal arm 13a of removable adapter 13.

Figure 4:
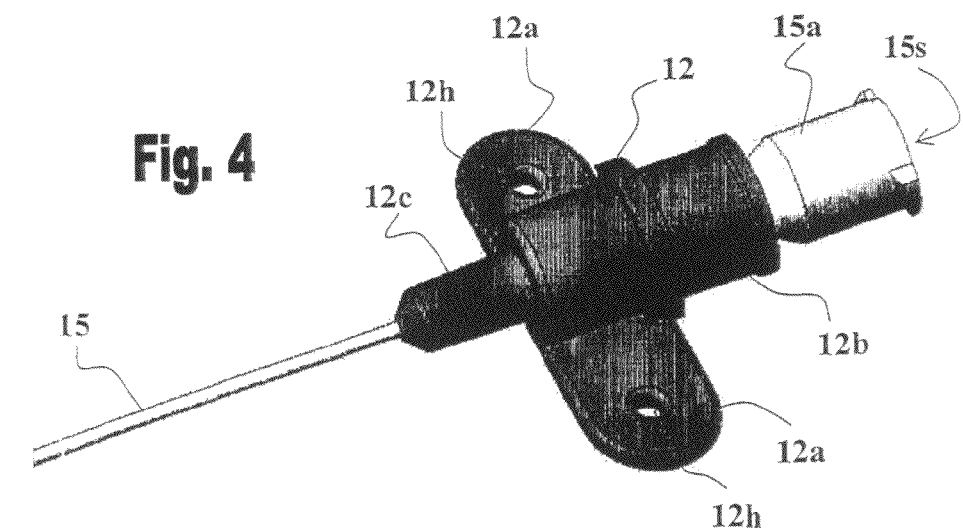
FIG. 4 shows the catheter device of the invention after removal of the adapter of the peelable introducer.

FIG. 2 shows the catheter insertion apparatus of the invention after removal of peelable introducer 14. In this state removable adapter 13 may be also removed by releasing its grip over distal connecting means 12c of inserter head 12, by retracting inserter head 12 proximally, and by removing catheter tube 15 passing through the passage provided in quick connector 13c and the apertures provided in distal arm 13a and proximal arm 13b, 13o and 13p, respectively, via the respective slits, 13e and 13f. For this purpose slit 13e may be provided in distal arm 13a connecting its upper side to aperture 13o, and slit 13f may be provided for connecting the upper side of proximal arm 13b and quick connector 13c attached to its outer side with aperture 13p in proximal arm 13b and the passage provided in quick connector 13c. FIG. 4 shows the catheter insertion apparatus of the invention after removal of the removable adapter 13 and flexible sleeve 11.

Flexible sleeve 11 may be manufactured by injection or blow molding from a flexible thermoplastic type of material, such as silicon rubber, AVA, polyethylene, preferably from silicone. The diameter of flexible sleeve 11 may generally be in the range of 6 to 30 mm, preferably about 10 mm, and its length may generally be in the range of 50 to 800 mm, preferably about 150 mm. Resilient portion 11b may be obtained by embedding a resilient element, such as a spring, in (or on) said section, or alternatively by forming suitable corrugations thereon, as exemplified in FIGS. 1A to 1C and in FIG. 2.

Inserter head 12 may be manufactured by injection molding from a suitable polymer type of material, such as silicone, AVA, polyethylene preferably from silicone. The diameter of inserter head 12 may generally be in the range of 3 to 20 mm, preferably about 10 mm. The diameter of proximal end portion 12b is adapted to be sealably and reversibly received in the proximal end opening of flexible sleeve 11. For example the diameter of proximal end portion 12b may generally be in the range of 4 to 15 mm, preferably about 8 mm, and its length may generally be in the range of 2 to 20 mm, preferably about 12 mm.

Similarly, the diameter of distal connecting means 12c is adapted to be sealably and reversibly received in the passage provided in quick connector 13c or directly into a proximal opening of peelable introducer 14 of a quick connection means provided thereon (not shown). For example, the diameter of distal connecting means 12c may generally be in the range of 2 to 10 mm, preferably about 4 mm, and its length may generally be in the range of 2 to 20 mm, preferably about 8 mm.

The diameter of the inner passage 12e provided in inserter head 12 should allow smooth passage of catheter tube 15 therethrough, while the diameter of its distal end portion is preferably slightly reduced to fit over the outer surface of the catheter tube 15 passing thereinside and thereby prevent backflow of fluids (e.g., blood). In addition, the fitting over catheter tube 15 obtained by the reduced diameter of inner passage 12e is further utilized to produce some friction force as may be required for holding catheter 15 in place while resilient/elastic portion 11b restores its shape after each advancement of the catheter tube. For example, the diameter of inner passage 12e may generally be in the range of 0.5 to 3 mm, preferably about 0.9 mm.

Removable adapter 13 may be manufactured by injection molding from a suitable rigid polymer type of material, such as polyethylene, polypropylene, ABS, preferably from polypropylene. The gap between distal arm 13a and proximal arm 13b may generally be in the range of 5 to 20 mm, preferably about 12 mm. The diameter of quick connector 13c may generally be in the range of 5 to 15 mm, preferably about 8 mm, and its length may generally be in the range of 2 to 15 mm, preferably about 6 mm. Base 13d of removable adapter may comprise an angled portion provided for facilitating the insertion of the introducer into the patient when said introducer is placed in removable adapter 13. The angle (θ, FIG. 1C) of angled portion of base 13d may generally be in the range of 15° to 65°, preferably about 30°.

The insertion of the catheter tube according to the present invention preferably comprises the following steps:

a) placing a peelable introducer 14 in removable adapter 13, and placing a piercing needle (not shown) in splittable sheath 14b by inserting it via aperture 13p, provided in proximal arm 13b, and advancing it distally until a distal section end thereof protrudes via the distal opening of splittable sheath 14b;

b) inserting splittable sheath 14b of introducer 14 into the body of the patient by means of piercing needle, and removing the piercing needle therefrom;

c) attaching flexible sleeve 11 and inserter head 12 assembly to removable adapter 13 by connecting the connecting means 12c of inserter head 12 to quick connector 13c of removable adapter 14;

d) advancing catheter tube 15, contained in flexible sleeve 11, into the body of the patient through the passage obtained between splittable sheath 14b, inserter head 12, and the interior of flexible sleeve 11;

e) optionally, after advancing the entire length of catheter tube 15, retaining catheter entry port 15a in socket 15s provided in the proximal end portion 12b of inserter head 12, thereby locking it in place in said hollow interior;

f) removing splittable introducer 14 by laterally pulling tearing tabs 14a;

g) removing removable adapter 13 by removing catheter tube 15 therefrom via slits 13e and 13f; and h) removing flexible sleeve 11 by pulling it proximally and releasing the grip of its distal end (11c) opening over proximal end portion 12b of inserter head 12.

It should be noted that peelable introducer 14 may comprise an integrated quick connection means or a suitable proximal end opening allowing the connection of connecting means 12c of inserter head 12 directly thereto. In such cases a modified design of removable adapter may be used wherein said removable adapter comprise distal arm 13a connected to base section 13d, without proximal arm 13b and quick connector 13c. Accordingly, if such modified removable adapter is used, step c) above should be modified accordingly such that connecting means 12c of inserter head 12 is connected directly to peelable introducer 14.

Figure 5:
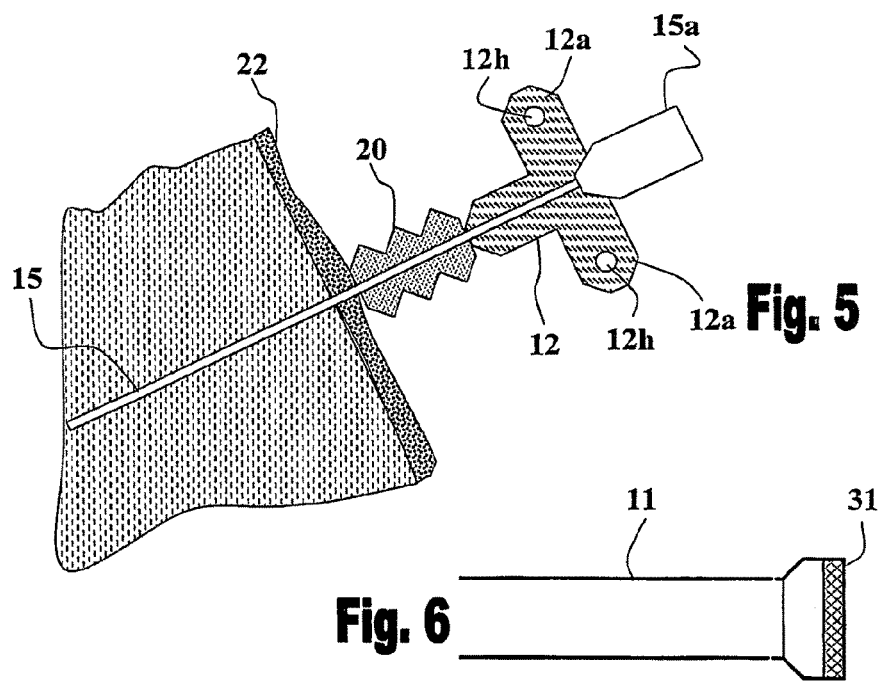
FIG. 5 schematically illustrates using a disinfecting element containing an antimicrobial substance placed around the catheter tube.

FIG. 5 schematically illustrates using a disinfecting element 20 containing an antimicrobial substance placed around the catheter tube 15. During the treatment carried out using catheter tube 15 disinfecting element 20 is pressed against the patient's skin 22 at the piercing site and thereby prevents bleeding and maintains a clean and substantially germ-free environment at the catheter insertion site. Disinfecting element 20 may be installed or manufactured as part of inserter head 12.

Disinfecting element 20 can be prepared from a flexible material, such as polyurethane, silicone, woven fabric, cellulose fiber, preferably from polyurethane containing an antimicrobial substance. Antimicrobial substance may be any type of disinfecting material as used today on the skin, or a type of impregnating polymer material as used for catheters manufacturing, preferably a polymer friendly material as chlorohexedine, silver cations, which may be introduced into disinfecting element 20 by impregnating it in the polymer manufacturing process or later on.

Figure 6:
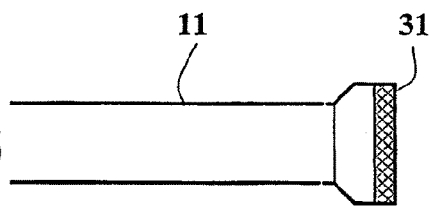
FIG. 6 schematically illustrates an implementation wherein the proximal end section of the flexible sleeve is sealed by a filter.

FIG. 6 shows an implementation wherein the proximal end section of the flexible sleeve 11 is sealed by a filter 31. In such implementation air may flow in and out of flexible sleeve 11, and thus prevent substantial pressure buildups therein during the catheter insertion steps, while preventing contamination of the interior of sleeve 11 due to filter 31 being a bacterial filter having pores size smaller then 0.22 Micron, or any other suitable filter made to any specific requirement. The filter can be made from Cellulose fiber, porous polyethylene or any other suitable material. Such pressure buildups may typically occur during the shortening of the length of resilient section 11b as portions of the catheter tube 15 are advanced distally due to the reduction of the inner volume of sleeve 11b.

Figure 7A:
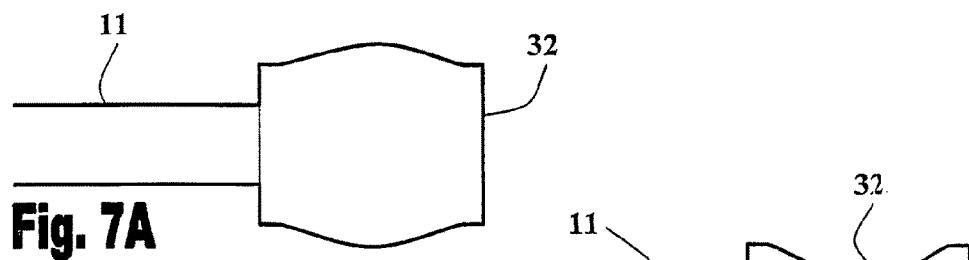
FIGS. 7A and 7B schematically illustrates a volume compensation mechanism for the flexible sleeve implemented by a compliant sleeve.
Figure 7B:
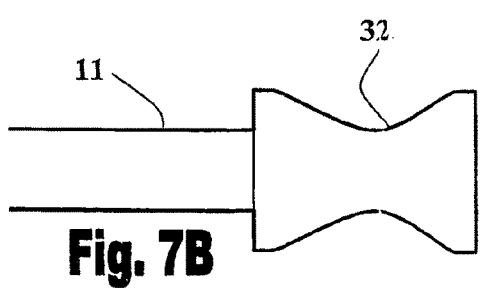

Another possible way to compensate such volume reductions and prevent pressure buildups in flexible sleeve 11 is by sealably embedding a compliant sleeve 32 in a section of flexible sleeve 11, as demonstrated in FIGS. 7A and 7B. FIG. 7A shows compliant sleeve 32 before resilient/elastic section 11b is pressed distally and FIG. 7B shows compliant sleeve 32 during the shortening of resilient/elastic section 11b. As demonstrated in FIGS. 7A and 7B, compliant sleeve 32 radially expands during the shortening of resilient/elastic section 11b, and thereby prevents substantial pressure buildups in flexible sleeve 11. When resilient/elastic section 11b restores its full length compliant sleeve 32 deflates and contracts radially.

Compliant sleeve 32 may be manufactured from flexible material, such as silicon, polyethylene, EVA, paper and Tyvak that might also act as a gas filter for sterilization by ETO, preferably from Silicon. Additionally or alternatively, a short and small plastic or paper bag sealably attached to the proximal end of sleeve 11 may be used instead, or together with, compliant sleeve 32 to prevent pressure buildups inside sleeve 11. The diameter of flexible sleeve may generally be in the range of 8 to 50 mm, preferably about 12 mm, and it length may generally be in the range of 5 to 150 mm, preferably about 100 mm. Compliant sleeve 32 may be an integral part of sleeve 11, or alternatively, it may be attached to flexible sleeve 11 by Gluing, or by means of dedicated connecting element, such as fasteners and/or suitable connectors.

Figure 8:
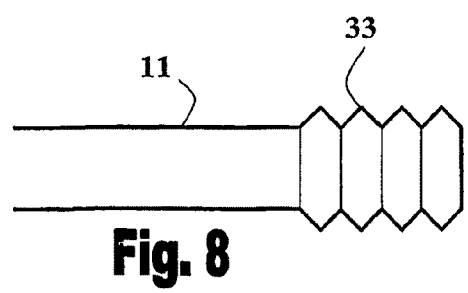
FIG. 8 demonstrates a volume compensation mechanism for the flexible sleeve implemented by a resilient or elastic sleeve.

FIG. 8 demonstrates a volume compensation mechanism implemented by a resilient sleeve 33 formed or sealably attached at the proximal end of flexible sleeve 11. In a similar fashion, the length of resilient sleeve 33 increases during the shortening of resilient/elastic section 11b when advancing portions of the catheter tube, and its length decreases when resilient/elastic section 11b restores its original length, thereby preventing pressure buildups in flexible sleeve 11.

Figure 9D:
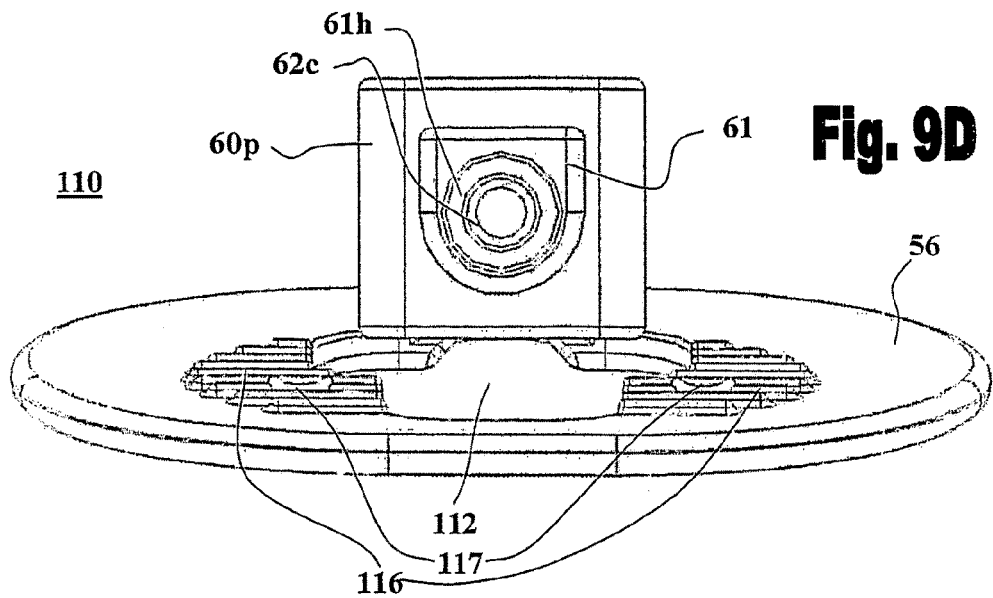
Figure 10A:
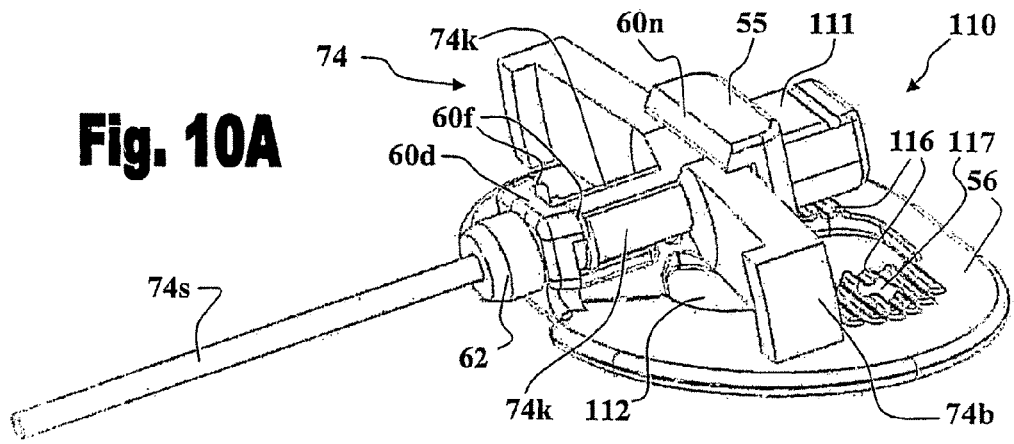
FIGS. 10A and 10B illustrates perspective and longitudinal-section views, respectively, of an assembly of a peelable introducer in the adapter shown in FIGS. 9A-9E.
Figure 10B:
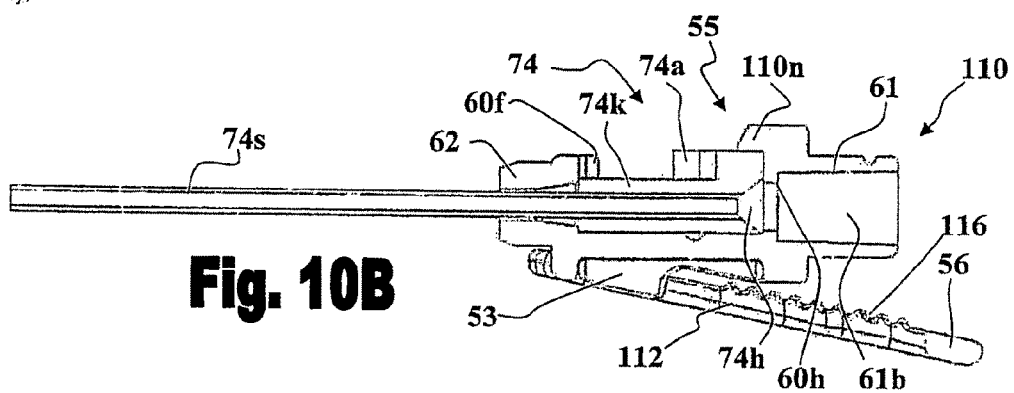

FIGS. 9A and 9B shows perspective and side views, respectively, of adapter 110 specially designed to receive a peelable introducer (74, FIGS. 10A and 10B). Adapter 110 comprises a base portion 56 and an introducer guard portion 55 connected to said base portion 56 by a flexible and relatively narrow connecting member 53. Adapter 110 is designed to receive a peelable introducer to be inserted into the body of a treated subject (not shown) by means of a piercing needle (90, FIGS. 17A and 17B) passed therethrough (e.g., over the needle technique), and after removal of said piercing needle, to connect to a catheter inserter (100, FIGS. 11A and 11B) by means of male connector (104b, FIG. 14B) provided on a head portion (inserter head 104) of said catheter inserter. After completing the catheter insertion procedure the catheter hub (58, FIGS. 12A and 12B) is securely attached to the inserter head (104) and the catheter inserter (100) is removed, leaving only said head portion (104) attached to adapter 110. Thereafter the peelable introducer (74) is securely split and removed.

As will described in detail hereinbelow, this design of adapter 110 substantially alleviates the catheter insertion procedure, efficiently secures the insertion steps of peelable introducer into the body of the treated subject and its removal therefrom, and allows insertion of the catheter tube through said peelable introducer while maintaining sterile surroundings. Adapter 110 securely holds the peelable introducer and prevents it from splitting inside the vessel of the treated subject while its splittable sheath (74s, FIGS. 10A and 10B) is inside the body of the treated subject. In addition, the unique design of adapter 110 further prevents the need to retract portions of the inserted catheter for allowing splitting the splittable introducer, and further prevents the need to insert the portions of the catheter tube after completing the splitting of the introducer.

Introducer guard portion 55 of adapter 60 comprises a proximal arm 60p, and a distal arm 60d, which are more or less parallel and being connected by base section 60b, thereby forming a "U"-like shaped portion. Proximal arm and distal arms, 60p and 60d, are configured to receive the peelable introducer 74 therebetween, and allow introducing said peelable introducer into the body of the treated subject by means of a piercing needle passed therethrough. Advantageously, proximal arm 60p and distal arm 60d are made bendable to allow easy assembly of the peelable introducer into the adapter 110.

Distal arm 60d comprises a sheath guard 62 provided on a distal face thereof. Sheath guard 62 is preferably a tubular member configured to securely hold splittable sheath 74s (shown on FIGS. 10A and 10B) of peelable introducer 74. The proximal arm 60p comprises connecting means 61 provided on the proximal face thereof for connecting adapter 110 to a catheter inserter device (100, FIG. 11A). Base portion 56 and introducer guard portion 55 of adapter 110 are connected by connecting member 53 such that an acute angle θ, generally in the range of 5° to 25°, preferably about 12°, is obtained therebetween. However, connecting member 53 is preferably made flexible enough to allow tilting introducer guard portion 55 about its connection to base portion 55 at connecting member 53 such that the angle θ between said portions can be adjusted according to the specific requirements of the procedure. Said requirements may depend, for example, on the body part on which said procedure is carried out, and on other specific properties of the treated subject as well. Adapter 110, is preferably made from a flexible or elastic material (e.g., silicon, EVA) allowing it to restore its original state after portions thereof were bent or stretched.

As shown in FIG. 9C, which shows a cross-longitudinal view of adapter 110, proximal arm 60p comprises an opening 61o provided in its distal face, said opening 61o opens into central bore 61b provided in connecting means 61. Central bore 61b is configured to sealably receive male connector 104b (shown in FIG. 14B) of head portion 104 of catheter inserter 100. As will be described in detail herein later central bore 61b is further used for accessing splittable sheath 74s (e.g., for placing a piercing needle therein, or for advancing a catheter tube therethrough) of peelable introducer 74 when it is assembled into adapter 110.

Distal arm 60d comprises a corresponding opening 62o (FIG. 9C) formed on its proximal face which opens into central bore 62b of sheath guard 62. Central bore 62b comprises a conical passage 62c, near opening 62o, which wall tapers distally towards the distal end of sheath guard 62. Conical passage 62c facilitates the assembly of peelable introducer 74 into adapter 110 by allowing insertion of the distal tip of splittable sheath 74s thereinto, while holding said peelable introducer 74 in a slanted state relative-to introducer guard portion 55. A similar insertion step is illustrated in FIG. 15C showing the assembly of a peelable introducer 74 into an adapter 60 according to another preferred embodiment of the invention.

After inserting the distal tip of splittable sheath 74s into conical passage 62c, splittable sheath 74s is advanced through central bore 62b until the distal tips of shanks 74k of peelable introducer 74 are pressed against the proximal face of distal arm 60d and securely held by fastening means 60f, provided on the upper rim of said distal arm 60d. Fastening means 60f are preferably implemented by a pair of horizontal protrusions which projects proximally towards proximal arm 60p, as shown in FIGS. 9A to 9C. After advancing splittable sheath 74s through central bore 62b and securing the distal tips of shanks 74k by fastening means 60f, the peelable introducer is snapped into introducer guard portion 55 by pressing splitting tabs 74a and 74b downwardly until an upper portion thereof is placed beneath snap 60n of proximal arm 60p. Peelable introducer 74 may be easily snapped into introducer guard portion 55 due to the flexibility of adapter 110, which allows bending it backwards at grooves 60g. Grooves 60g may be provided on the upper side of base section 60b and/or on it lateral sides.

Snap 60n is preferably implemented by a horizontal extension (e.g., 1 to 5 mm) of proximal arm 60p which protrudes distally towards distal arm 60d. Advantageously, a portion of snap 60n facing distal arm 60d is angled to assist the step in which splitting tabs 74a and 74b are slid into introducer guard 55. To further facilitate the assembly of peelable introducer 74 into introducer guard 55 base section 60b is provided with lateral and/or upper grooves 60g which add flexibility thereto and thus allow bending the proximal portion of base section 60b, comprising proximal arm 60p, with relative ease.

The distal end of central bore 61b includes an annular fastener 61h, which is preferably a short end portion of central bore 61b having an inner diameter smaller than the inner diameter of central bore 61b, for example, the difference between said inner diameters may be about 0.5 mm. Annular fastener 61h is configured to receive and hold male connector 104b of inserter head 104 (FIG. 14B) and thereby provide a sealed and secured connection between catheter inserter 100 and peelable introducer 74 via connecting means 61 of adapter 110.

FIGS. 10A and 10B are perspective and cross-longitudinal views, respectively, of adapter 110 having peelable introducer 74 assembled thereinto. As shown in FIG. 10B, peelable sheath 74s of peelable introducer 24 may be accessed via central bore 61b and annular fastener 61h which communicates with tapering passage 74h. Tapering passage 74h is a short passage which tapers distally towards the proximal end of splittable sheath 74s, thereby providing improved accessibility thereinto and sealable connection with male connection 104b of inserter head 104 (FIG. 14B).

Figure 9E:
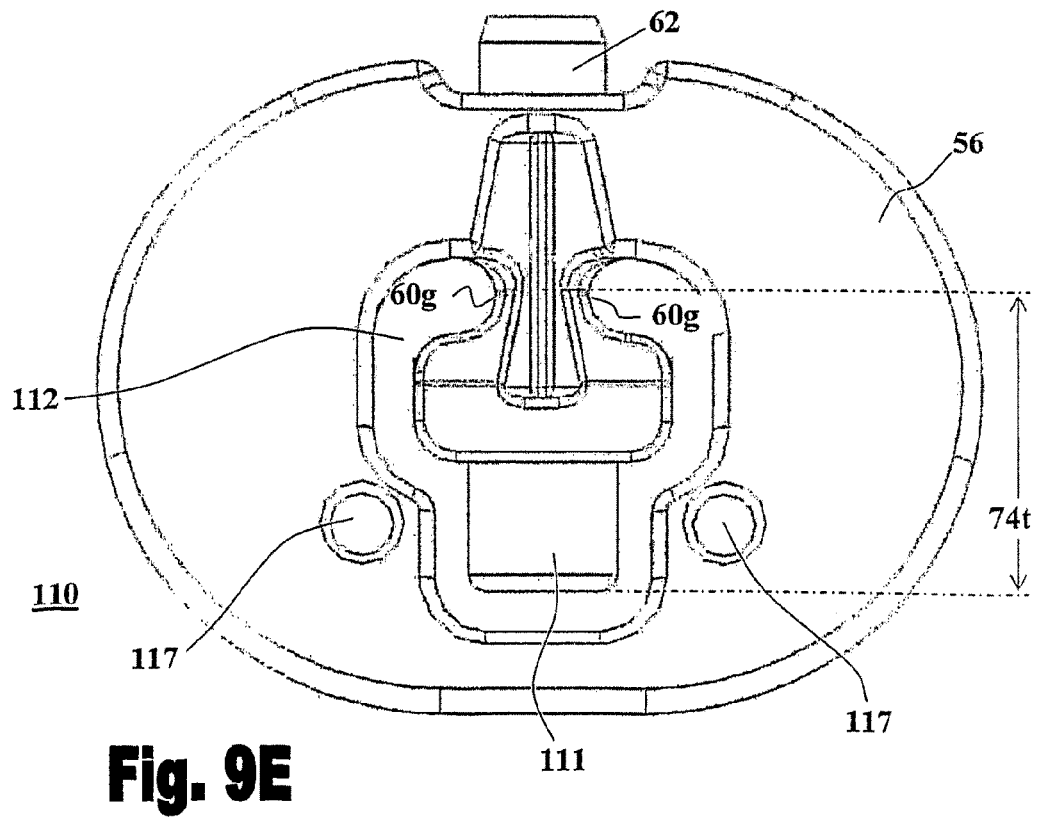

As best seen in the bottom view of adapter 110, shown in FIG. 9E, base portion 56 of, adapter 110 advantageously includes a central hole 112, which is preferably configured in a shape corresponding to the shape of the proximal portion 74t of introducer guard 55, comprising the proximal portion of base section 60b, proximal arm 60p and connecting means 61 attached to its proximal face. Central hole 112 allows bending the proximal portion 74t of introducer guard 55 downwardly therethrough and improves the ability of the operator to maneuver said proximal portion 74t about grooves 60g.

Base portion 56 may further include gripping enhancement surfaces 116 formed of the upper surface thereof for improving the ability to grip and fixate adapter 110 in place while assembling peelable introducer 74 thereinto and during the catheter insertion procedure. Gripping enhancement surfaces 116 may be implemented by several aligned elevations formed on the upper surface area of base portion 56. Base portion 56 may further include lateral holes 117 which may be used for fixating adapter 110 in place, by sutures for example.

Figure 11A:
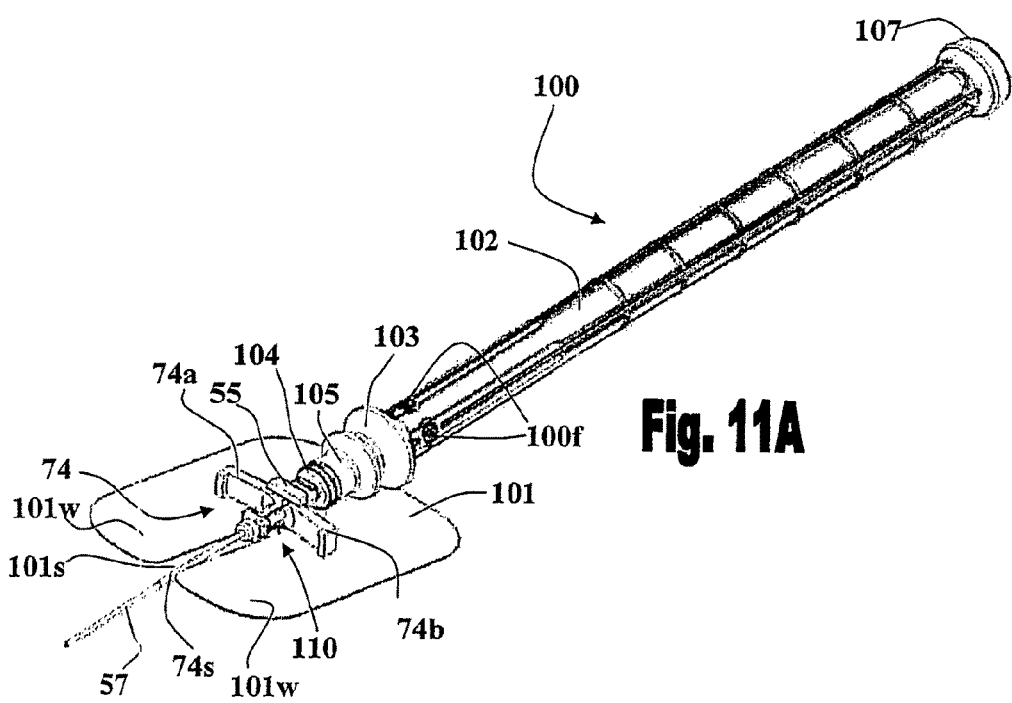

FIG. 11A shows an assembly of adapter 110 and peelable introducer 74 when connected to catheter inserter 100, comprising flexible sleeve 102 and catheter tube 57 contained thereinside. As demonstrated in FIG. 11A, adapter 110 may be anchored to the body of the treated subject (not shown) by an adhesive patch 101. Adhesive patch 101 preferably comprises a slit 101s which forms two lateral wings 101w in adhesive patch 101. Slit 101s is made wide enough to permit conveniently introducing connecting member 53 of adapter 110 between wings 101w, thereby allowing adhesive patch to entirely cover the upper surface of base portion 56 and thus improve the anchoring of adapter 110 in place.

With reference to FIG. 11B, showing a cross-longitudinal view of the assembly shown in FIG. 11A, flexible sleeve 102 of catheter inserter 100 comprises a resilient/elastic portion 103 which is used during the step of inserting catheter tube 57 for advancing portions of catheter tube 57 into the body of the treated subject. During this step the practitioner grasps portions of catheter tube 57 by pressing fingers portions 100f (FIG. 11A) of flexible sleeve 100 thereover and pushing, the same distally, such that resilient/elastic portion 103 of flexible sleeve 100 is pressed distally against adapter 110, thereby advancing portions of catheter tube 57 distally. After releasing the grip over flexible sleeve 100 flexible portion 103 thereof restores its original shape and returns the pushed sleeve backwardly back to its previous state. In this way portions of catheter tube 57 are advanced into the body of the treated subject until its distal tip reaches a desired location, typically by advancing the entire length thereof.

The distal end 105 of flexible sleeve 102 is configured to tightly fit over inserter head 104 which is used for connecting catheter inserter 100 to adapter 110. As better seen in the cross-longitudinal view shown in FIG. 11B, inserter head 104 comprise a central passage 104p through which catheter tube 57 is advanced during the insertion step. As best seen in FIG. 14B, the connection between inserter head 104 and adapter 110 is achieved by male connector 104b, formed on the distal portion of inserter head 104 and designed to provide a sealable and secure connection with connecting means 61. Male connector 104b is designed to sealably fit into central bore 61b of connecting means 61, and provide the required sealed connection by means of an annular groove 55a formed on its outer surface, said annular groove 55a is configured to receive annular fastener 61h provided in central bore 61b of connecting means 61.

As best seen in FIG. 11B, the lumen of catheter tube 57 can be accessed via catheter hub 58 provided at the proximal end thereof. Catheter hub 58 comprises an access port 58b having a male adapter 58a formed on its distal section and configured to sealably and securely fit into socket 104s provided in the proximal portion of inserter head 104. With reference to FIGS. 12A and 12B, wherein a perspective and a cross-longitudinal views, respectively, of the assembly of FIG. 11A are shown without the flexible sleeve 100, male adapter 58a of catheter port 58 comprises an annular groove 58d configured to receive an annular protrusion 104a provided in central passage 104p of inserter head 104.

Figure 13:
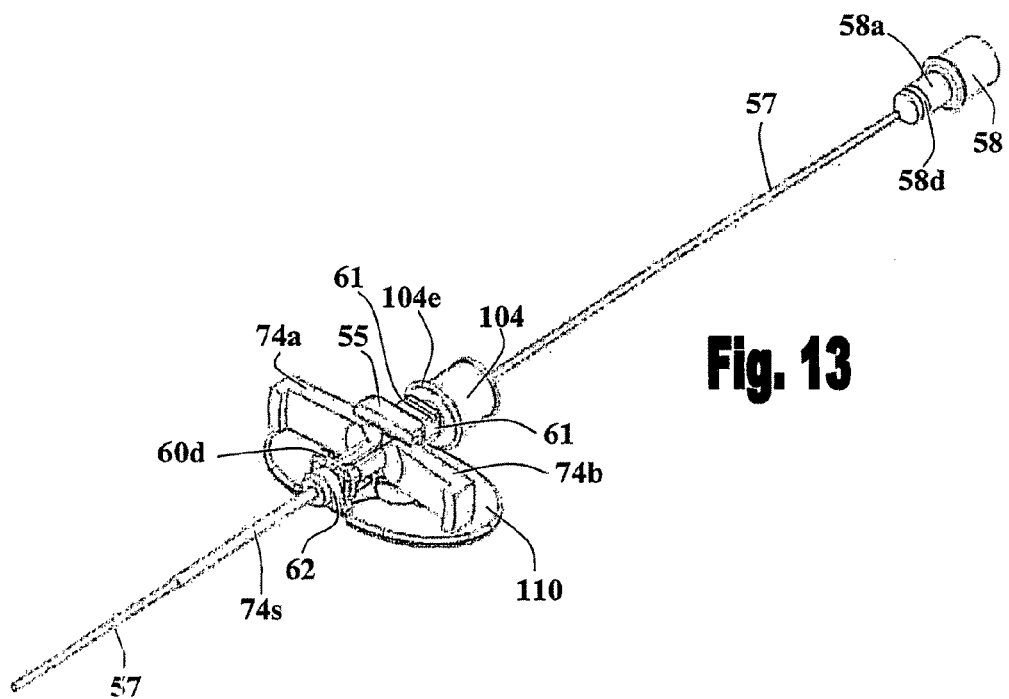
FIG. 13 illustrates the assembly illustrated in FIGS. 12A-12B without a fastening adhesive patch.

For the sake of clarity, FIG. 13 provides a perspective view of the assembly shown in FIG. 11, but without flexible sleeve 100 and without adhesive patch 101. Typically, after completing the insertion of catheter tube 57 into the body of the treated subject, male adapter 58a of catheter hub 58 is securely and sealably fitted into socket 104s provided in the proximal portion of inserter head 104, and flexible sleeve 102 is then removed by retracting it proximally and thereby releasing the connection between distal end 105 of flexible sleeve 102 and the outer surface of the proximal section of inserter head 104.

Figure 14A:
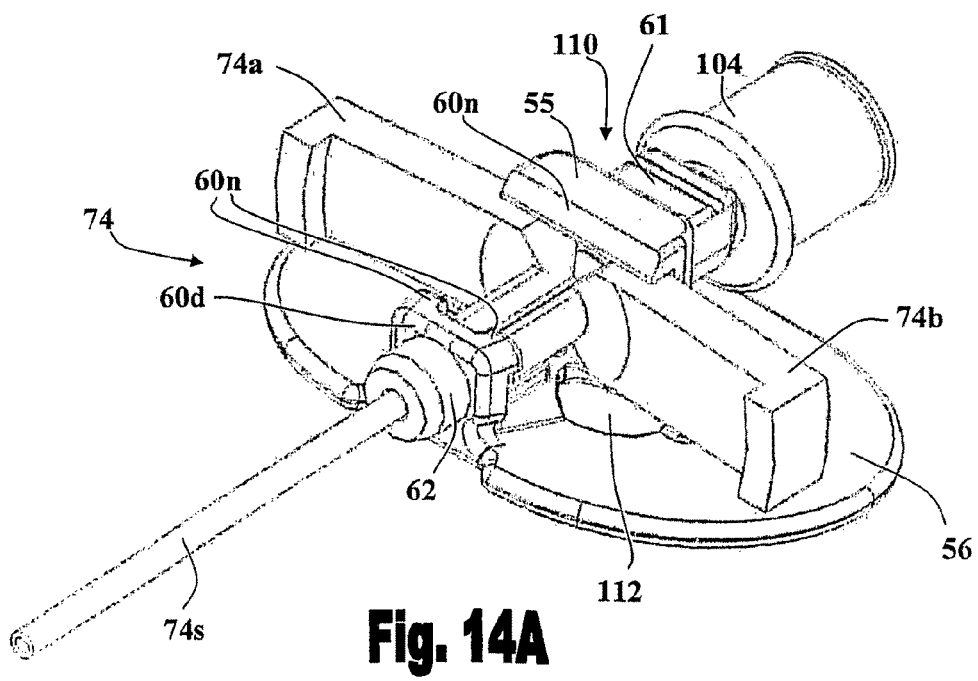
FIGS. 14A and 14B illustrates perspective and longitudinal-section views, respectively, of an assembly of the adapter shown in FIGS. 9A-9E with a peelable introducer and an inserter head.
Figure 14B:
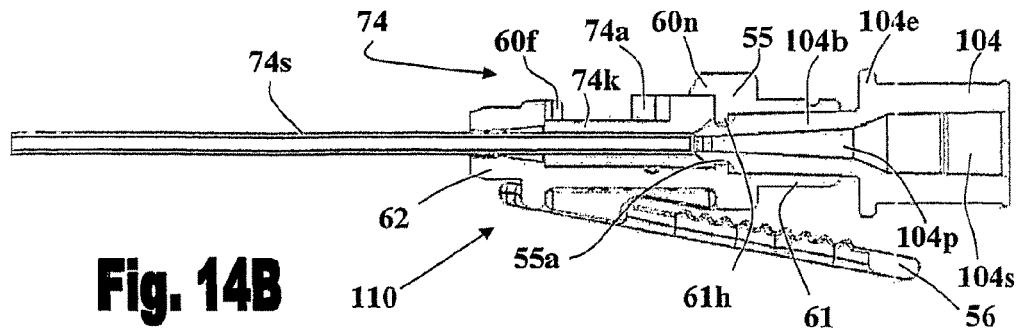

FIGS. 14A and 14B show perspective and cross-longitudinal views, respectively, of adapter 110 having peelable introducer 74 assembled thereinto, and inserter head 104 connected to its connecting means 61.

Figure 15A:
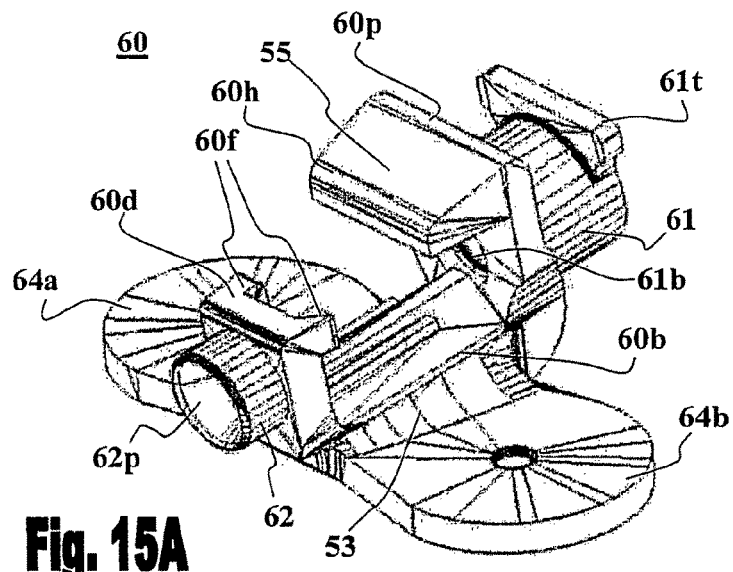
FIGS. 15A and 15B illustrates perspective and longitudinal-section views, respectively, of an adapter for a peelable introducer according to another preferred embodiment of the invention.
Figure 15B:
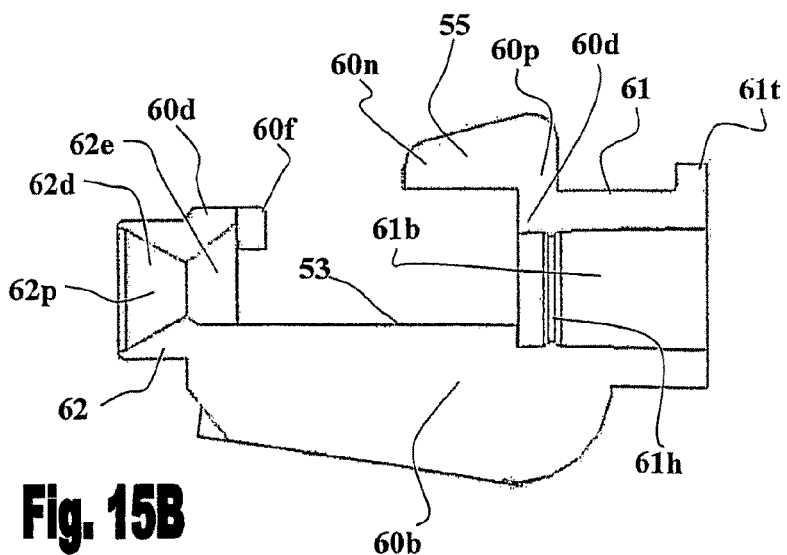

FIGS. 15A and 15B show a perspective and cross-longitudinal views of another preferred embodiment for an adapter 60 of the invention designed to receive a peelable introducer and connect to a catheter inserter. Adapter 60 includes an introducer guard portion 55 comprising a distal arm 60d and a proximal arm 60p, connected by a base section 60b, substantially similar in structure to adapter 110 previously described hereinabove with reference to FIGS. 9 to 14. Base section 60b of said introducer guard portion 55 is connected via connecting member 53 to lateral wings 64a and 64b, used for fixating adapter 60 to the body of the treated subject. Preferably, connecting member 53 is made flexible enough to allow tilting introducer guard portion 55 about its connection to base portion 55 at connecting member 53.

The structure and functionality of the members of adapter 60 are substantially similar to the corresponding members of adapter 60 designated by the same numerals and discussed with reference to FIG. 9 to 14, and therefore they will not be discussed herein again for the sake of brevity. For example, as in the previously described embodiment distal arm 60d comprises fastening means 60f and proximal arms comprises snap 60n, designed to receive and hold peelable introducer 74. Said distal arm 60d also includes a similar sheath guard 62, and said proximal arm includes similar connecting means 61.

However, various differences between adapters 110 and 60 do exist, and will be now discussed with reference to FIGS. 15 to 18.

Referring now to FIG. 15B, wherein a cross-longitudinal view of adapter 60 is shown, the passage 62p provided in sheath guard 62 comprises a conical distal portion 62d which tapers proximally towards the distal arm 60d. The proximal side 62e of passage 62p is configured such that the upper wall of said passage comprises a section which tapers distally, thereby forming a passage 62p which diameter is gradually reduced from both ends towards its center. Passage 62p is configured so in order to facilitate the assembling of peelable introducer 74 into adapter 60, as will be now explained.

Referring now FIG. 15C, showing a cross-longitudinal view of adapter 60 having a portion of splittable sheath 74s of peelable introducer 74 passed via passage 62p. As illustrated in FIG. 15C, the slanted sections, 62d and 62e, of passage 62p permits insertion of splittable sheath 74s into passage 62p simply by advancing it thereinto in a slanted state relative to the longitudinal axis of adapter 60. The assembly of peelable introducer 74 into adapter 60 is completed by fastening the distal tips of shanks 74k of peelable introducer 74 under fastening means 60f and pushing splitting tabs 74a and 74b downwardly until an upper portion thereof is placed beneath snap 60n of proximal arm 60p. A perspective view of adapter 60 having peelable introducer 74 assembled thereinto is shown in FIG. 16.

FIGS. 17A and 17B schematically illustrates perspective and longitudinal-section views, respectively, of an assembly of a peelable introducer 74 fitted into the adapter 60, and having piercing needle 90 connected thereto. Piercing needle 90 is connected to this assembly by passing its needle 90n via the passage provided by central bore 61b into splittable sheath 74s. Typically, when the entire length of needle 90n is placed in this assembly, a short distal portion of needle 90n protrudes distally from the distal end opening of splittable sheath 74s. Piercing needle comprises a handle 90h provided at the proximal end of needle 90, where said handle 90h includes a clasp 90f formed on the distal end of said handle 90h and configured to securely fit over and hold fastening tongue 61t formed on the upper surface of connecting means 61, near its proximal edge.

FIG. 18 shows a perspective view of the assembly of peelable introducer 74, adapter 60, and piercing needle 90, wherein the splittable sheath 74s of peelable introducer 74 is covered by a needle guard assembly 93 designed to tightly fit over sheath guard 62.

Adapters 110 and 60 may be manufactured by means of press or injection molding, from a type of flexible material, such as but not limited to Silicon, EVA, flexible polyethylene, flexible polypropylene, preferably from EVA. The gap between distal (60d) and proximal (60p) arms is configured to receive the shanks (74k) of peelable introducer, which by way of example, may be in the range of 6 to 25 mm. The length of sheath guard 62 may generally be in the range of 2 to 10 mm, preferably about 5 mm, and its outer diameter may be about 2 to 10 mm. The length of connecting means 61 may generally be in the range of 4 to 12 mm, preferably about 7 mm, and the internal diameter of central bore 61*b* provided therein may be about 4 to 7 mm.

Figure 19A:
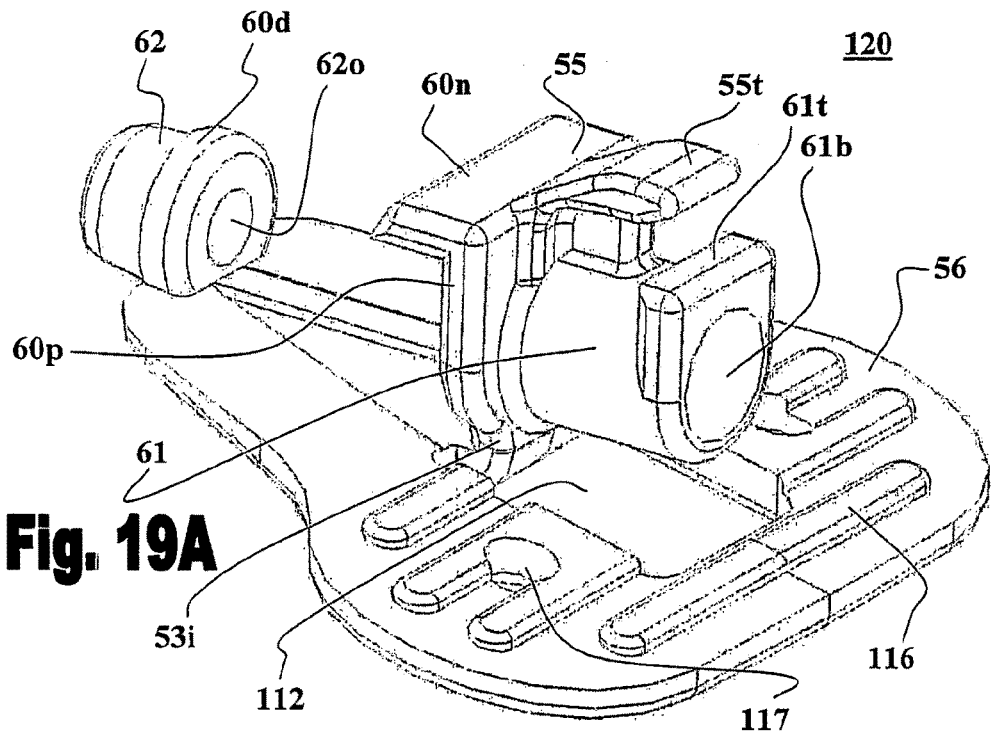
FIG. 19A illustrates a perspective view of yet another preferred embodiment of the adapter for a peelable introducer according to the invention.

FIG. 19A illustrates a perspective view of yet another preferred embodiment of an adapter 120 for a peelable introducer according to the invention. In principle, adapter 120 comprises elements having similar structure and functionality, as in the adapter (110) described herein above with reference to FIGS. 9A-9B, and which are thus designated by the same numeral. Adapter 120 includes a "U"-like shaped section configured to hold the proximal portion of a removable introducer, but in this case said arm are connected by a distal section of base portion 56. Proximal arm 60*p* is connected to base portion 56 by means of a flexible/elastic member 53*i*, thereby allowing tilting said proximal arm 60*p* about said flexible/elastic member 53*i*. Base portion 56 comprises central hole 112 formed such that connecting means 61 provided on the outer side of proximal arm 60*p* may pass therethrough whenever distal arm 60*p* is tilted proximally.

Figure 19B:
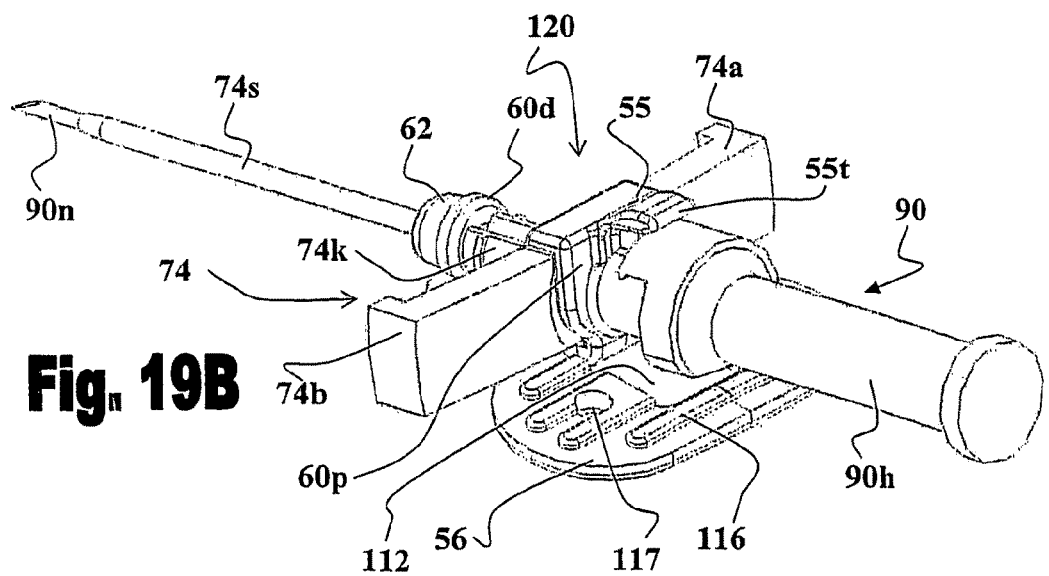
FIG. 19B illustrates an assembly of the peelable introducer fitted into the adapter shown in FIG. 19A, and a piercing needle passing therethrough.

Adapter 120 further comprises fastening tongue 61*t* formed on the upper surface of connecting means 61, near its proximal edge for fastening handle 90*h* of piercing needle 90 thereto by fitting clasp 90*f* formed on the distal end of said handle 90*h*. Said handle 90*h* is further secured to adapter 120 by means of horizontal tongue 55*t* protruding proximally from the upper side of proximal arm 60*p*. FIG. 19B illustrates an assembly of peelable introducer 74 fitted into adapter 120, and including a piercing needle 90 passing therethrough.

Figure 20A:
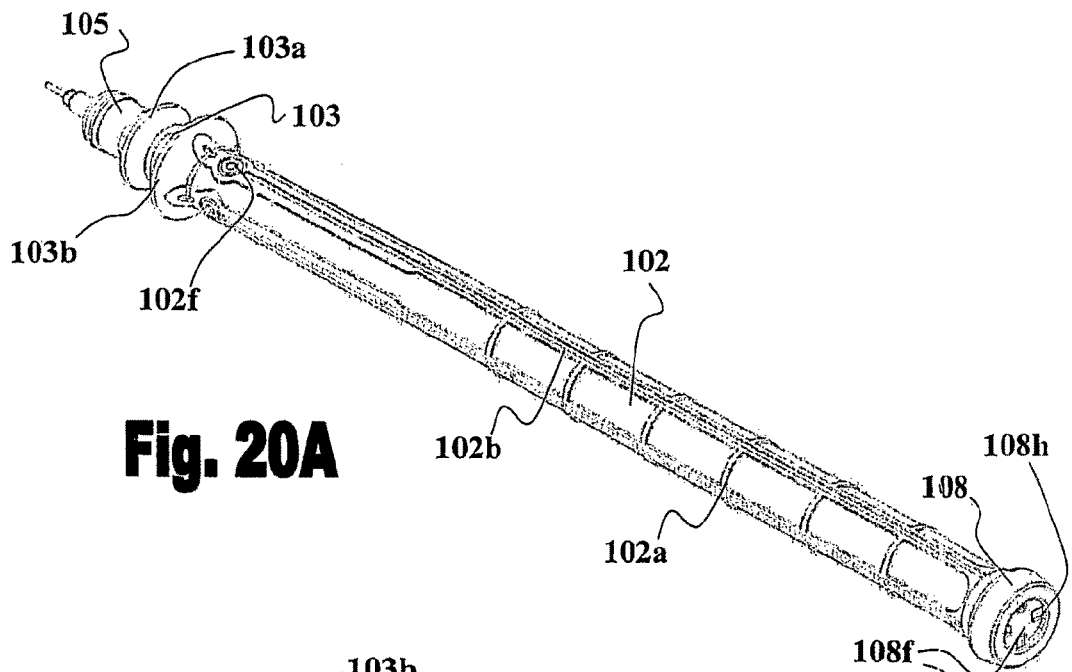
FIGS. 20A and 20B show perspective and longitudinal-section views, respectively, of a preferred embodiment of the flexible sleeve.

FIG. 20A shows a perspective view of a flexible sleeve 102, according to one preferred embodiment of the invention. Flexible sleeve 102 comprises annular and longitudinal supports, 102*a* and 102*b*, respectively, which provide flexible sleeve 102 improved structural stability (helps to prevent collapses and folds thereof). In this preferred embodiment proximal end 108 of flexible sleeve 102 is sealed by a filtering means 108*f*.

Figure 20B:
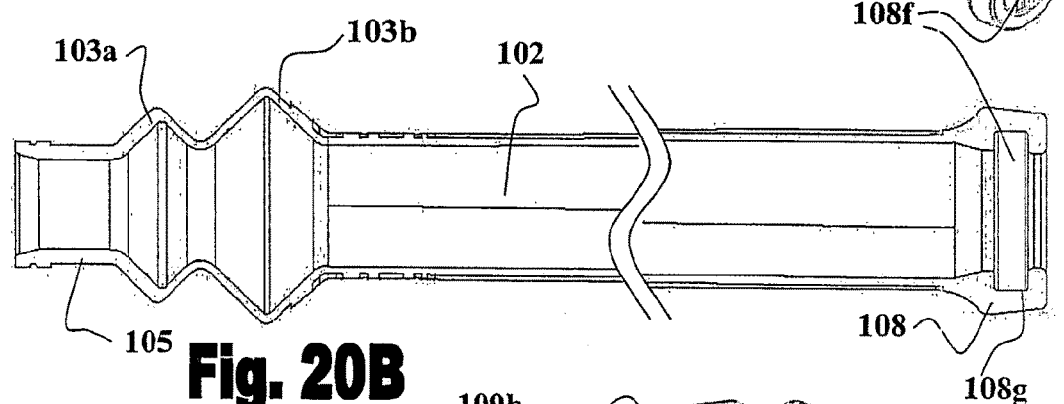

As best seen in the longitudinal view shown in FIG. 20B, proximal end of flexible sleeve 102 is comprises and inner annular groove 108*g* wherein filtering means 108*f* is fitted.

Resilient/elastic portion 103*b* of flexible sleeve 102 is formed to include annular corrugations 103*a*, 103*b*, and in this way facilitate the catheter insertion procedure by allowing to push portions of catheter tube 57 distally by externally gripping the same via flexible sleeve 102 and compressing resilient/elastic portion 103*b* distally, thereby shortening the length of resilient/elastic portion 103*b*.

In order to prevent kinking of resilient/elastic portion 103*b* the diameter of corrugations 103*a* and 103*b* is gradually increased distally, namely, the diameter of annular corrugation 103*a* (e.g., ~16 mm) is smaller than the diameter of annular corrugation 103*b* (e.g., ~20 mm). Moreover, as can be seen in FIG. 20B, the thickness of at least a portion of distal annular corrugation 103*b* is made thicker (e.g., ~1.3 mm) than the thickness of flexible sleeve 102 along its length (e.g., ~0.7 mm). This configuration assures that the contractions of resilient/elastic portion 103*b*, during advancements of flexible tube 57, are axial and uniform relative to sleeve 102.

Filtering means 108*f* is preferably a type of dust or bacterial filter (e15 micron mesh disc filter, 0.22 fier filter) which allows passage of air into flexible sleeve 102 while preventing contamination thereof. Most preferably, filtering means 108*f* is a type tortuous path filter, based on the bacterial barrier principle, based on the principle wherein bacteria, as well as other pathogens, drifting in air, can only travel in approximately straight lines. In the preferred embodiment of the invention filtering means 108*f* is implemented by a rigid component (e.g., a disc) comprising tortuous grooves 108*h* communicating with the internal space of flexible sleeve 102. In this way, by closing proximal end 108 of flexible sleeve 102 with filtering means 108*f*, having at least one tortuous groove 108*h*, the air introduced into flexible sleeve 102 is passed via the bacterial barrier formed by the tortuous path of said at least one tortuous groove 108*h*.

Figure 20C:
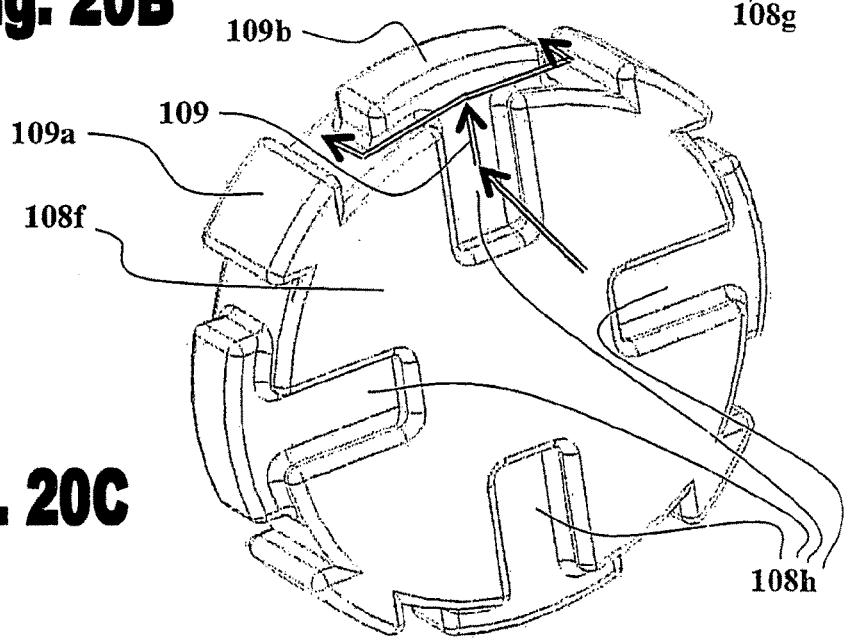
FIG. 20C is a perspective view of a preferred embodiment of the filtering means.

FIG. 20C is a perspective view of a preferred embodiment of the filtering means 108*f*, wherein said, filtering means 108*f* is implemented by a disk comprising circumferential shoulders 109*a* and tongues 109*b*, which are formed such that a tongue 109*b* is placed between each neighboring shoulders 109*a*. Tortuous paths (designated by arrow 109) are provided by forming air paths starting in the grooves (108*g*) formed on the outer face of filter element 108*f*, said grooves communicate with a channel formed by having the thickness of tongues 109 slightly smaller (e.g., ~2 mm) than the thickness of filter means 108*f* (e.g., ~3 mm), wherein said channel communicates with the inner space of flexible sleeve via the gap provided between tongues 109*b* and shoulders 109*a*.

Filter means 108*f* may be manufactured by injection molding, from a resilient polymer of material, preferably from polypropylene. The width of the air channels (109) in filter means 108*f* is generally in the range of 1 to 4 mm, preferably about 1.5 mm, for allowing free flow of air in and out of flexible sleeve 102, and the air path formed by them is configured such that the air passing therethrough undergo several significant direction changes, thus preventing bacteria and other pathogens travel into flexible sleeve 102. The diameter of filtering means 108*f* is configured to allow fitting in tightly in annular groove 108*g* provided flexible sleeve 102, e.g., in the range of 10 to 20 mm, preferably about 16 mm, and the width of filtering means 108*f* is generally in the range of 1 to 7 mm, preferably about 3 mm. The number and dimensions of tortuous grooves 108*h* is preferably designed to allow unrestricted air flow, such that volume changes in flexible sleeve during the catheter insertion process will cause substantial pressure buildups.

Figure 21:
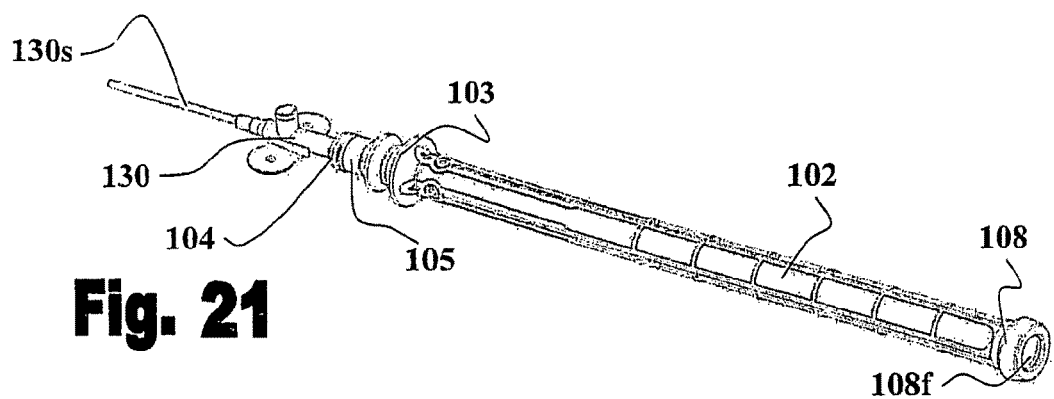
FIG. 21 illustrates an assembly of the catheter insertion apparatus of the invention with a conventional catheter introducer device.

FIG. 21 illustrates an assembly of the catheter insertion apparatus of the invention with a conventional catheter introducer device 130. In this assembly, flexible sleeve 102 and the inserter head 104, attached to the distal end 105 of said flexible sleeve 102, are connected directly to the conventional catheter introducer device 130. In this case, however, the cannula 130*s* of introducer 130 stays in the patient body throughout the catheterization process. Accordingly, after completing the catheter insertion step and removing flexible sleeve 102, male adapter 58*a* (FIG. 22) of catheter hub 58 is inserted and secured in the socket 104*s* provided in the proximal portion of inserter head 104, such that the assembly comprising catheter introducer device 130 and inserter head 104 with catheter hub 58 remains on the body of the patient.

Figure 22:
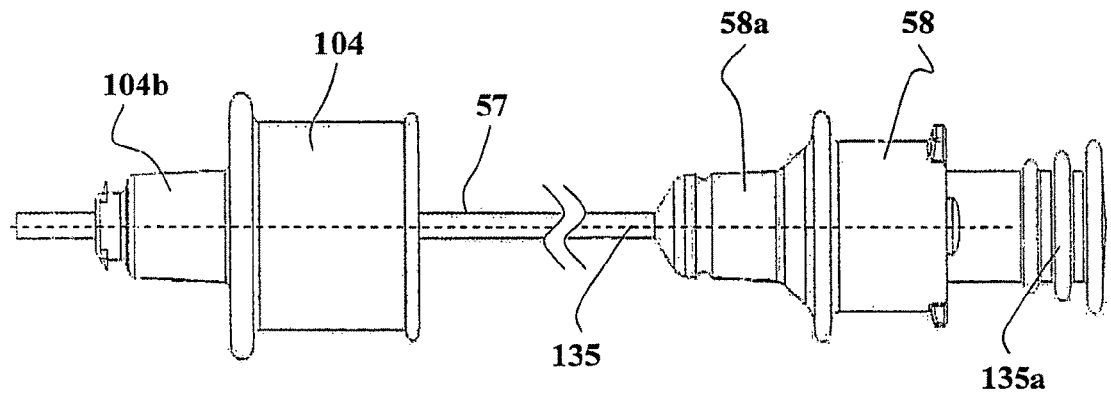
FIG. 22 illustrates the catheter tube with a stiffening guide-wire passed thereinside.

FIG. 22 illustrates the catheter tube 57 with a stiffening guide-wire 135 passed thereinside, said stiffening guide-wire 135 comprises a gripping member 135*a* at its proximal end. The main object of stiffening guide-wire 135 and its gripping member 135*a* is to sealably fill the lumens of catheter tube 57 and of access port 58*b* (FIG. 12B) of catheter hub 58, to exclude any air from it and facilitate the insertion of catheter tube 57 without air thereinside. Guide-wire 135 may be manufactured from a flexible material, such as, but not limited to, stainless still, titanium, nylon or polypropylene, preferably from nylon.

It should be noted that the embodiments exemplified in the Figs. are not intended to be in scale and are in diagram form to facilitate ease of understanding and description.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different tubes adapters, connectors, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A catheter insertion system comprising a catheter introducer device comprising an introducer sheath, said system comprising: a catheter containment unit in which a catheter tube comprising a catheter entry port hub is held, said catheter containment unit comprises an opening adapted to sealably and reversibly connect to an inserter head, said inserter head is adapted to sealably and reversibly connect, and provide said catheter tube passage, to said catheter introducer device, wherein said catheter containment unit comprises at least one flexible portion and an elastic/resilient portion located near its opening for advancing portions of said catheter tube through said passage, and wherein said inserter head comprises a socket which is adapted to sealably receive a distal end portion of said catheter hub in the socket thereby sealing its inner passage such that catheter containment unit can be removed by pulling it proximally and releasing its attachment to said inserter head.

2. The catheter insertion system according to claim 1, wherein the catheter introducer device is held by an adapter having hollow connecting means adapted for connecting it to the inserter head and for providing passage therethrough into the introducer sheath of said catheter introducer device.

3. The catheter insertion system according to claim 1, further comprising a stiffening guide-wire removably placed in, to fill, the lumen of the catheter tube.

4. The catheter insertion system according to claim 2, wherein the catheter introducer device is a type of removable catheter introducer device.

5. The catheter insertion system according to claim 4, wherein the catheter introducer device is a peelable introducer.

6. The catheter insertion system according to claim 2, wherein the adapter comprises a "U"-like shaped portion having substantially parallel distal and proximal arms, each of which having an inner and outer sides, said arms are connected by a base and comprise opposing apertures, and wherein said "U"-like shaped portion is adapted to receive and hold the catheter introducer device such that the proximal portion of said catheter introducer device is held by said arms, at least a portion of the introducer sheath of said introducer device is passed through the aperture provided in said distal arm, and the interior of said introducer sheath is accessible via the aperture provided in said proximal arms of said "U"-like shaped portion.

7. The catheter insertion system according to claim 6, wherein the distal and/or proximal arms of the "U"-like shaped portion further comprises retaining means for holding the introducer device.

8. The catheter insertion system according to claim 6, wherein the aperture provided in the distal arm of the "U"-like shaped portion is adapted to prevent the splitting of the portion, or entire length, of the introducer sheath passed therethrough.

9. The catheter insertion system according to claim 6, wherein the hollow connecting means are provided on the outer side of the proximal and/or distal arms for allowing sealably and reversibly connection thereto while providing passage therethrough to/from the apertures provided in said proximal arms.

10. The catheter insertion system according to claim 6, wherein the proximal and distal arms of the "U"-like shaped portion of the adapter further comprise slits passing from an upper side thereof and connected to the apertures provided in said arms.

11. The catheter insertion system according to claim 9, wherein the hollow connecting means comprise a corresponding slit passing from an upper side thereof and connected to their hollow interiors.

12. The catheter insertion system according to claim 6, wherein the base connecting the arms of the "U"-like shaped portion comprises lateral, upper, and/or lower, grooves for increasing its elasticity/flexibility.

13. The catheter insertion system according to claim 9, wherein the passage through the aperture in the distal arm and the interior of the hollow connecting means connected to the outer side of the distal arm is distally tapering.

14. The catheter insertion system according to claim 9, wherein at least a portion of the passage through the hollow interior of the connecting means connected on the outer side of the distal arm tapers proximally.

15. The catheter insertion system according to claim 6, wherein the adapter further comprises a base portion or wings to which said "U"-like shaped portion is connected.

16. The catheter insertion system according to claim 15, wherein the connection between said base portion or wings and said "U"-like shaped portion is achieved by means of an elastic or flexible member allowing reversibly tilting said "U"-like shaped portion thereabout.

17. The catheter insertion system according to claim 1, wherein the catheter containment unit further comprise filter means for allowing passage of air to/from its interior.

18. The catheter insertion system according to claim 17, wherein the filtering means is a type tortuous path filtering means.

19. The catheter insertion system according to claim 1, wherein the catheter containment unit further comprises a compliant or corrugated portion adapted to expand in response to pressure buildups in said catheter containment unit, and to restore its shape whenever said pressure buildup are released.

20. The catheter insertion system according to claim 1, wherein the size and/or thickness of a distal portion of the elastic/resilient portion of the catheter containment device is made smaller than the size/thickness of the proximal portion thereof.

21. The catheter insertion system according to claim 1, wherein a disinfecting element containing an antimicrobial substance is placed over a portion of the catheter tube adjacent to the insertion site.

22. A method for inserting a catheter tube by means of a catheter introducer device having an introducer sheath, comprising:
- placing the introducer sheath in the body of the treated subject by means of a piercing needle and removing said piercing needle therefrom thereafter;
- connecting a catheter containment unit to said catheter introducer device by means of an inserter head reversibly connected to an opening of said catheter containment unit, said catheter containment unit comprises a catheter tube having a catheter entry port hub, wherein said inserter head comprises a socket and is adapted to sealably receive a distal portion of said catheter entry port hub in the socket;
- advancing said catheter tube into the body of the treated subject by manually pushing said catheter tube distally via said catheter containment unit;
- retaining said catheter entry port hub in said socket provided in said inserter head; and
- removing said catheter containment unit by pulling it proximally and releasing its grip over said inserter head.

23. A method for inserting a catheter tube by means of a catheter introducer device having an introducer sheath, comprising:
- placing said catheter introducer device in an adapter having hollow connecting means adapted for connecting it to an inserter head and for providing passage therethrough into said introducer sheath of said catheter introducer device;
- placing the introducer sheath in the body of the treated subject by means of a piercing needle and removing said piercing needle therefrom thereafter;
- connecting a catheter containment unit to said catheter introducer device by means of an inserter head reversibly connected to an opening of said catheter containment unit, wherein said catheter containment unit comprises a catheter tube having a catheter entry port hub, wherein said inserter head comprises a socket and is adapted to sealably receive a distal portion of said catheter entry port hub in the socket;
- advancing said catheter tube into the body of the treated subject by manually pushing said catheter tube distally via said catheter containment unit;
- retaining said catheter entry port hub in said socket provided in said inserter head; and
- removing said catheter containment unit by pulling it proximally and releasing its grip over said inserter head.

24. A method according to claim 23, wherein the adapter comprises a "U"-like shaped portion adapted to receive and hold the catheter introducer device.

25. A method according to claim 24, wherein the catheter introducer device is a type of removable catheter introducer device, and wherein said catheter insertion device is removed after completing the catheter insertion steps by splitting portions of the introducer sheath within the "U"-like shaped portion.

26. A method according to clam 23, wherein the catheter tube comprises a stiffening guide-wire filling the lumen thereof, said stiffening guide-wire is removed therefrom after removal of the catheter containment unit.

27. A catheter containment unit for advancing a catheter tube comprising a catheter entry port hub contained therein, the catheter containment unit comprising: an opening adapted to sealably and reversibly receive an inserter head comprising a socket, said inserter head is adapted to sealably and reversibly connect, and provide said catheter tube passage, to a catheter introducer device, at least one flexible portion and an elastic/resilient portion located near its opening for advancing portions of said catheter tube through said passage, wherein said inserter head is adapted to sealably receive a distal end portion of said catheter hub in the socket.

28. The catheter containment unit according to claim 27, wherein the size and/or thickness of a distal portion of the elastic/resilient portion of the catheter containment device is made smaller than the size/thickness of the proximal portion thereof.

29. The catheter containment unit according to claim 27, further comprising filtering means for allowing air to flow thereinto, while preventing contamination of its interior.

30. An adapter for receiving a peelable introducer comprising: a base portion, and an introducer guard portion connected to said base portion by a flexible and substantially narrow connecting member;
- said introducer guard portion comprises bendable proximal and distal arms which are substantially parallel and are connected by a second base portion;
- wherein said distal arm comprises a tubular member sheath guard provided on its distal face thereof, and an opening formed on its proximal face which opens into a central bore of said sheath guard;
- wherein said proximal arm comprises connecting means provided on its proximal face thereof, and an opening provided in its distal face, said opening opens into a central bore provided in said connecting means.

31. An adapter according to claim 30 wherein the distal arm comprises fastening means provided on the upper rim of said distal arm.

32. An adapter according to claim 31 wherein the fastening means are a pair of horizontal protrusions which project proximally towards the proximal arm.

33. An adapter according to claim 30 wherein the proximal arm comprises a snap wherein said snap is a horizontal extension the proximal arm which protrudes distally towards the distal arm.

* * * * *